(12) United States Patent
Whiting et al.

(10) Patent No.: US 11,666,215 B2
(45) Date of Patent: Jun. 6, 2023

(54) MOBILE MONITORING AND PATIENT MANAGEMENT SYSTEM

(71) Applicant: ZOLL Medical Corporation, Chelmsford, MA (US)

(72) Inventors: Jason T Whiting, Gibsonia, PA (US); Gary A Freeman, Waltham, MA (US); Thomas E Kaib, Irwin, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

(21) Appl. No.: 17/810,912

(22) Filed: Jul. 6, 2022

(65) Prior Publication Data

US 2022/0330822 A1    Oct. 20, 2022

Related U.S. Application Data

(63) Continuation of application No. 17/113,271, filed on Dec. 7, 2020, now Pat. No. 11,419,496, which is a
(Continued)

(51) Int. Cl.
| | | |
|---|---|---|
| *A61B 5/00* | (2006.01) | |
| *A61N 1/39* | (2006.01) | |
| *A61N 1/372* | (2006.01) | |
| *G16H 50/20* | (2018.01) | |
| *G16H 20/30* | (2018.01) | |

(Continued)

(52) U.S. Cl.
CPC .......... *A61B 5/0015* (2013.01); *A61B 5/6805* (2013.01); *A61B 5/742* (2013.01);
(Continued)

(58) Field of Classification Search
CPC ....... A61B 5/0015; A61B 5/021; A61B 5/024; A61B 5/11; A61B 5/14542; A61B 5/14551; A61B 5/6805; A61B 5/742; A61B 5/746; A61M 16/0051; A61M 16/021; A61M 2205/3375; A61M 2205/3553;
(Continued)

(56) References Cited

U.S. PATENT DOCUMENTS

| | | |
|---|---|---|
| 4,928,690 A | 5/1990 | Heilman et al. |
| 5,078,134 A | 1/1992 | Heilman et al. |

(Continued)

*Primary Examiner* — Nader Bolourchi
(74) *Attorney, Agent, or Firm* — ZOLL Medical Corporation

(57) ABSTRACT

A patient management system for providing patient queues of patient reports to users includes communications circuitry configured to receive first physiological information from monitoring medical devices being worn by a first plurality of patients and receive second physiological information from therapeutic medical devices being worn by a second plurality of patients. Each of the monitoring medical devices is configured to sense one or more predetermined physiological parameters of its respective patient. Each of the therapeutic medical devices is configured to monitor its respective patient for a predetermined physiological condition and provide a treatment. The patient management system also includes at least one processor configured to prepare a plurality of monitoring patient reports, prepare a plurality of therapeutic patient reports, generate a patient queue based on the pluralities of monitoring and therapeutic patient reports, and provide the patient queue to an end user computing device via the communications circuitry.

20 Claims, 16 Drawing Sheets

Related U.S. Application Data continuation of application No. 16/511,359, filed on Jul. 15, 2019, now Pat. No. 10,905,327, which is a continuation of application No. 16/158,682, filed on Oct. 12, 2018, now Pat. No. 10,395,765, which is a continuation of application No. 15/157,995, filed on May 18, 2016, now Pat. No. 10,127,357.

(60) Provisional application No. 62/163,000, filed on May 18, 2015.

(51) Int. Cl.
| | | |
|---|---|---|
| *G06Q 50/22* | (2018.01) | |
| *G16H 10/60* | (2018.01) | |
| *G16H 40/67* | (2018.01) | |
| *G16H 10/65* | (2018.01) | |
| *A61B 5/021* | (2006.01) | |
| *A61B 5/11* | (2006.01) | |
| *A61B 5/024* | (2006.01) | |
| *A61B 5/145* | (2006.01) | |
| *A61B 5/1455* | (2006.01) | |
| *A61M 16/00* | (2006.01) | |

(52) U.S. Cl.
CPC ....... *A61N 1/37247* (2013.01); *A61N 1/3904* (2017.08); *A61N 1/3925* (2013.01); *A61N 1/39044* (2017.08); *A61N 1/3993* (2013.01); *G06Q 50/22* (2013.01); *G16H 10/60* (2018.01); *G16H 10/65* (2018.01); *G16H 20/30* (2018.01); *G16H 40/67* (2018.01); *G16H 50/20* (2018.01); *A61B 5/021* (2013.01); *A61B 5/024* (2013.01); *A61B 5/11* (2013.01); *A61B 5/14542* (2013.01); *A61B 5/14551* (2013.01); *A61B 5/746* (2013.01); *A61M 16/0051* (2013.01); *A61M 16/021* (2017.08); *A61M 2205/3375* (2013.01); *A61M 2205/3553* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2209/088* (2013.01); *A61M 2230/04* (2013.01); *A61M 2230/06* (2013.01); *A61M 2230/201* (2013.01); *A61M 2230/205* (2013.01); *A61M 2230/30* (2013.01); *A61M 2230/42* (2013.01); *A61M 2230/50* (2013.01); *A61M 2230/63* (2013.01); *A61M 2230/65* (2013.01)

(58) Field of Classification Search
CPC .. A61M 2205/3569; A61M 2205/3584; A61M 2205/3592; A61M 2205/505; A61M 2205/52; A61M 2209/088; A61M 2230/04; A61M 2230/06; A61M 2230/201; A61M 2230/205; A61M 2230/30; A61M 2230/42; A61M 2230/50; A61M 2230/63; A61M 2230/65; A61N 1/37247; A61N 1/3904; A61N 1/39044; A61N 1/3925; A61N 1/3993; G06Q 50/22; G16H 10/60; G16H 10/65; G16H 20/30; G16H 40/67; G16H 50/20
See application file for complete search history.

(56) References Cited

U.S. PATENT DOCUMENTS

| | | |
|---|---|---|
| 5,741,306 A | 4/1998 | Glegyak et al. |
| 5,944,669 A | 8/1999 | Kaib |
| 6,065,154 A | 5/2000 | Hulings et al. |
| 6,225,901 B1 | 5/2001 | Kail, IV |
| 6,253,099 B1 | 6/2001 | Oskin et al. |
| 6,280,461 B1 | 8/2001 | Glegyak et al. |
| 6,569,095 B2 | 5/2003 | Eggers |
| 6,602,191 B2 | 8/2003 | Quy |
| 6,622,050 B2 | 9/2003 | Thompson |
| 6,669,630 B1 | 12/2003 | Joliat et al. |
| 6,681,003 B2 | 1/2004 | Linder et al. |
| 6,708,057 B2 | 3/2004 | Morganroth |
| 6,976,958 B2 | 12/2005 | Quy |
| 7,002,468 B2 | 2/2006 | Eveland et al. |
| 7,212,850 B2 | 5/2007 | Prystowsky et al. |
| 7,353,179 B2 | 4/2008 | Ott et al. |
| 7,685,005 B2 | 3/2010 | Riff et al. |
| 7,715,905 B2 | 5/2010 | Kurzweil et al. |
| 7,907,996 B2 | 3/2011 | Prystowsky et al. |
| 8,032,631 B2 | 10/2011 | Iino et al. |
| 8,078,270 B1 | 12/2011 | Webb et al. |
| 8,185,623 B2 | 5/2012 | Lewis et al. |
| 8,204,580 B2 | 6/2012 | Kurzweil et al. |
| 8,219,608 B2 | 7/2012 | Alsafadi et al. |
| 8,271,082 B2 | 9/2012 | Donnelly et al. |
| 8,290,574 B2 | 10/2012 | Feild et al. |
| 8,332,233 B2 | 12/2012 | Ott et al. |
| 8,369,944 B2 | 2/2013 | Macho et al. |
| 8,425,414 B2 | 4/2013 | Eveland |
| 8,438,039 B2 | 5/2013 | Gottesman et al. |
| 8,473,039 B2 | 6/2013 | Michelson et al. |
| 8,483,807 B2 | 7/2013 | Kurzweil et al. |
| 8,583,221 B1 | 11/2013 | Patel et al. |
| 8,620,418 B1 | 12/2013 | Kuppuraj et al. |
| 8,769,153 B2 | 7/2014 | Dziubinski |
| 8,798,734 B2 | 8/2014 | Kuppuraj et al. |
| 8,945,019 B2 | 2/2015 | Prystowsky et al. |
| 8,954,137 B2 | 2/2015 | Kurzweil et al. |
| 8,983,587 B2 | 3/2015 | Kurzweil et al. |
| 9,044,148 B2 | 6/2015 | Michelson et al. |
| 9,081,884 B2 | 7/2015 | Kuppuraj et al. |
| 10,384,066 B2 | 8/2019 | Whiting et al. |
| 2004/0034284 A1 | 2/2004 | Aversano et al. |
| 2016/0246943 A1 | 8/2016 | Lake et al. |
| 2020/0128073 A1 | 4/2020 | Savage et al. |

| Type | Patient Name | DOB | Treating Physician | Treatment Provided |
|------|--------------|-----------|--------------------|--------------------|
| T | Smith, J. | 5/6/1950 | Garcia | 1 |
| T | Jones, M. | 7/12/1962 | Miller | 0 |
| T | Brown, B. | 4/3/1945 | Garcia | 0 |

MOBILE MONITORING AND PATIENT MANAGEMENT SYSTEM

CROSS REFERENCE TO RELATED APPLICATIONS

This application is a continuation of U.S. patent application Ser. No. 17/113,271, filed Dec. 7, 2020, entitled "Mobile Monitoring and Patient Management System," which is a continuation of U.S. patent application Ser. No. 16/511,359, filed Jul. 15, 2019, entitled "Mobile Monitoring and Patient Management System," now U.S. Pat. No. 10,905,327, which is a continuation of U.S. patent application Ser. No. 16/158,682, filed Oct. 12, 2018, entitled "Mobile Monitoring and Patient Management System," now U.S. Pat. No. 10,395,765, which is a continuation of U.S. patent application Ser. No. 15/157,995, filed May 18, 2016, entitled "Mobile Monitoring and Patient Management System," now U.S. Pat. No. 10,127,357, which claims priority to U.S. Provisional Patent Application No. 62/163,000, filed May 18, 2015, entitled "Mobile Monitoring and Patient Management System," the disclosures of each of which are hereby incorporated by reference in their entireties.

TECHNICAL FIELD

The present disclosure relates to a patient management system for receiving and displaying physiological information from mobile medical devices such as therapeutic and monitoring medical devices.

BACKGROUND

There are a wide variety of electronic and mechanical devices for monitoring and treating patients' medical conditions. In some examples, depending on the underlying medical condition being monitored or treated, medical devices such as cardiac pacemakers or defibrillators may be surgically implanted or connected externally to the patient.

One of the most deadly cardiac arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia.

Implantable or external pacemakers and defibrillators (such as automated external defibrillators or AEDs) have significantly improved the ability to treat these otherwise life-threatening conditions. Such devices operate by applying corrective electrical pulses directly to the patient's heart. For example, bradycardia can be corrected through the use of an implanted or external pacemaker device. Ventricular fibrillation can be treated by an implanted or external defibrillator.

Continuous monitoring devices operate by substantially continuously monitoring the patient's heart for treatable arrhythmias and, when such is detected, the device applies corrective electrical pulses directly to the heart. Wearable pacing devices and/or defibrillators have been developed for a certain population of patients, e.g., those that may have recently experienced a heart attack, that are susceptible to heart arrhythmias and are at temporary risk of sudden death, or that are awaiting an implantable device. For example, to protect against cardiac arrest and other cardiac health ailments, some at-risk subjects may use a non-invasive bodily-attached ambulatory medical monitoring and treatment device, such as the LifeVest® wearable cardioverter defibrillator available from ZOLL® Medical Corporation. To remain protected, the subject wears the device nearly continuously while going about their normal daily activities, while awake, and while asleep.

Non-therapeutic monitoring medical devices, e.g., cardiac event monitors, collect cardiac information, such as a patient electrocardiogram (ECG) recordings, and provide the information to an external network or remote server on a periodic basis. Mobile cardiac telemetry devices monitor patient physiological information, such as ECG, and can send data aperiodically, such as when a particular triggering event is identified.

SUMMARY

Non-limiting examples of embodiments will now be described.

In an example, a patient management system is provided. The patient management system can comprise: communications circuitry configured to receive first physiological information relating to a first at least one patient from at least one therapeutic medical device and second physiological information relating to a second at least one patient from at least one monitoring medical device; and a computing device, optionally, comprising a user interface, the user interface configured to display at least one of the first and second physiological information according to a user selection.

The at least one therapeutic medical device can comprise at least one of: a portable defibrillator, a wearable defibrillator, a cardiac pacing device, a portable ventilator, a cardiopulmonary resuscitation system, and combinations thereof.

The at least one monitoring medical device can comprise at least one of: a mobile cardiac monitoring device, a patient weight monitor, a blood glucose monitor, a pulse oximeter, a blood pressure monitor, and a patient movement detector.

The first physiological information can comprise whether a treatment was delivered to the first at least one patient, and the second physiological information can comprise cardiac information of the second at least one patient.

The computing device can be configured to run one or more instances of an application for viewing patient reports based on the received first and second physiological information. A first instance of the application is configured to display information based on the first physiological information and a second instance is configured to display information based on the second physiological information.

The computing device can be further configured to launch a first instance of an application when the user selection comprises a selection to display the first physiological information. The computing device can also be configured to launch a second instance of the application when the user selection comprises a selection to display the second physiological information.

The user configuration can comprise user action involving at least one of: selecting to display first and second physiological information; selecting to display first physiological information and not second physiological information; and selecting to display second physiological information and not first physiological information.

The at least one monitoring medical device can be configured to permit the patient to enter one or more patient symptoms. The patient symptoms can comprise at least one of: a skipped beat, shortness of breath, light headedness, racing heart rate, fatigue, fainting, chest discomfort, weakness, dizziness, and/or giddiness.

The at least one monitoring medical device is configured to permit the patient to an activity level of the patient. The activity level of the patient comprising at least one of: resting, light activity, moderate activity, and rigorous activity.

The at least one monitoring medical device is configured to identify one or more events, the identified events comprising at least one of: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations.

The user interface can be configured to allow a user to view the received first and second physiological information based at least in part on one or more of the user's role, the user's location, a profile of one or more of the plurality of patients, and an underlying characteristic of the received physiological information.

The user interface can be further configured to allow the user to customize a manner in which at least a portion of the received physiological information is presented. The user interface can also be configured to allow the user to specify one or more alerts relating to the at least one of patient symptom information and patient-related event information. The user can specify that the one or more alerts should be sent to another recipient other than the user. The user interface can also be configured to allow the user to delegate access to at least a portion of the received information to another user.

The at least one therapeutic medical device can be configured to operate in both a therapeutic mode and a monitoring mode. The at least one therapeutic medical device can comprise a plurality of monitoring elements configured to operate in both the therapeutic mode and the monitoring mode, and a plurality of therapeutic elements configured to operate only in the therapeutic mode.

The at least one monitoring medical device can be configured to operate in both a therapeutic mode and a monitoring mode. The at least one monitoring medical device can comprise a plurality of monitoring elements configured to operate in both the therapeutic mode and the monitoring mode, and a plurality of therapeutic elements configured to operate only in the therapeutic mode.

In another example, a patient management system can comprise: communications circuitry configured to receive physiological information relating to a plurality of patients from a plurality of medical devices, the physiological information, optionally, comprising at least one of patient symptom information and patient-related event information; and a computing device comprising a user interface, the user interface configured to allow a user to triage at least a portion of the received physiological information based, at least in part, on at least one of patient symptom information and the patient-related event information.

The medical devices can be configured to permit the patient to manually enter the patient symptoms.

The patient symptoms can comprise at least one of: a skipped beat, shortness of breath, light headedness, racing heart rate, fatigue, fainting, chest discomfort, weakness, dizziness, and/or giddiness.

The patient symptoms can further comprise an activity level of the patient comprising at least one of: resting, light activity, moderate activity, and rigorous activity.

The identified events can comprise at least one of: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations.

In another example, a patient management system can comprise: communications circuitry configured to receive physiological information relating to a plurality of patients from a plurality of medical devices, the physiological information, optionally, comprising at least one of patient symptom information and patient-related event information; and a computing device comprising a user interface, the user interface configured to allow a user to view the received physiological information based at least in part on one or more of: a) the user's role; b) the user's location; c) a profile of one or more of the plurality of patients; and d) an underlying characteristic of the received physiological information.

The user interface can be configured to allow the user to customize a manner in which at least a portion of the received physiological information is presented.

The user interface can be configured to allow the user to specify one or more alerts relating to the at least one of patient symptom information and patient-related event information.

The user can specify that the one or more alerts should be sent to another recipient other than the user.

The user interface can be configured to allow the user to delegate access to at least a portion of the received information to another user.

In an example, a mobile patient monitoring system can comprise: a plurality of therapeutic medical devices each comprising communication circuitry and being configured to be connected to one of a first subset of patients to obtain physiological information for the patient; a plurality of monitoring medical devices each comprising communication circuitry and being configured to be connected to one of a second subset of patients to obtain physiological information for the patient; a communications network configured to transmit the physiological information about the first subset of patients from the plurality of therapeutic medical devices and the physiological information about the second subset of patients from the plurality of monitoring medical devices; and a computing device comprising a user interface configured to receive the physiological information for the first subset of patients and the second subset of patients over the communications network and to provide the information to a user. The user interface can be configured to selectively display physiological information from at least one of the first subset of patients and the second subset of patients based on a selection from the user.

The selection from the user can comprise at least one of: selection to display information from both the first subset of patients and the second subset of patients; selection to display information for the first subset of patients and not information for the second subset of patients; and selection to display information for the second subset of patients and not information for the first subset of patients.

The therapeutic medical device can comprise at least one of: a portable defibrillator, a wearable defibrillator, a cardiac pacing device, a portable ventilator, a cardiopulmonary resuscitation system, and combinations thereof.

Information received from the physiological information can comprise an electrocardiogram for the patient.

The physiological information received from the first subset of patients can further comprise information about a number of treatments provided to the patient by the therapeutic medical device.

The user interface can be configured to provide an alert to the user, the alert being based on analysis of the received physiological information.

In another example, a mobile patient monitoring system can comprise: a plurality of medical devices each comprising communication circuitry and being configured to obtain physiological information from a patient, wherein the physiological information includes one or more patient symptoms and/or one or more identified events; a communications network; and a computing device comprising a user interface configured to receive the physiological information from the plurality of medical devices and to selectively display the information from one or more of the plurality of medical devices in an order based, at least in part, on the patient symptoms and/or the identified events.

The medical device can be configured for the patient to manually enter the patient symptoms.

The patient symptoms can comprise at least one of: a skipped beat, shortness of breath, light headedness, racing heart rate, fatigue, fainting, chest discomfort, weakness, dizziness, and/or giddiness. The patient symptoms can further comprise an activity level of the patient at least one of: resting, light activity, moderate activity, and rigorous activity.

The identified events can comprise at least one of: atrial fibrillation, bradycardia, tachycardia, atrio-ventricular block, Lown-Ganong-Levine syndrome, atrial flutter, sinoatrial node dysfunction, cerebral ischemia, syncope, atrial pause, and/or heart palpitations.

In another example, a system for customizing physiological information received from a medical device can comprise: at least one medical device comprising communication circuitry and connected to a patient for obtaining physiological information for the patient; and a computing device comprising a user interface and at least one processor configured to perform instructions for receiving the physiological information from the at least one medical device, and displaying at least a portion of the received physiological information with the user interface in an order based, at least in part, on a selection by a user.

The physiological information can comprise an electrocardiogram of the patient.

Displaying at least a portion of the received physiological information can comprise: receiving the selection from the user, wherein the selection comprises at least one information field, populating the information field with values based, at least in part, on the received physiological information, and displaying the populated information field to the user with the user interface.

The at least one information field can comprise at least one of: patient total wear time, percentage of time in atrial fibrillation, percentage of time with bradycardia, percentage of time with tachycardia, average heart rate, most common symptom reported by the patient, number of identified events, and a number of treatments by a therapeutic medical device.

The order for displaying physiological information received from the plurality of medical devices can be determined based on values of the populated information fields for each patient.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings.

DETAILED DESCRIPTION OF THE INVENTION

Figure 1:
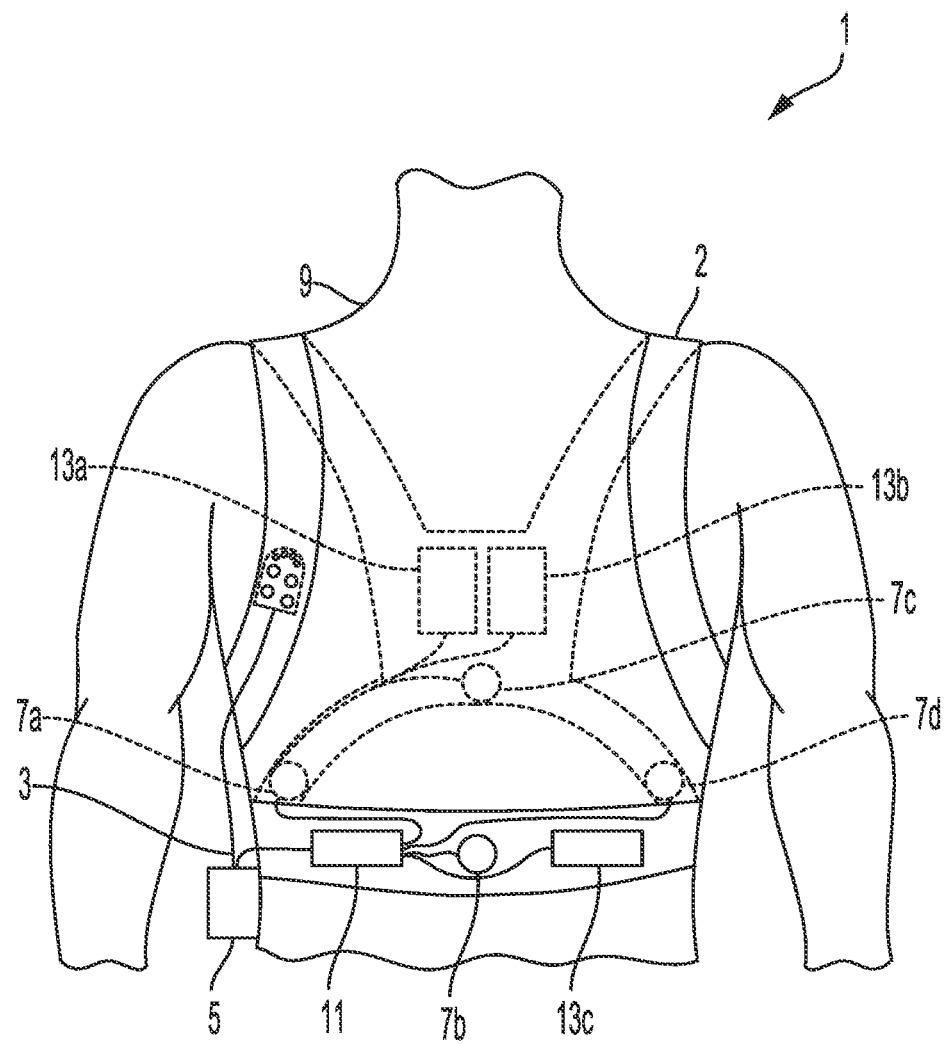
FIG. 1 depicts a wearable medical device, in accordance with an example of the present disclosure.

As used herein, the singular form of "a", "an", and "the" include plural referents unless the context clearly dictates otherwise.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

This disclosure relates to systems and techniques for receiving and displaying physiological information from therapeutic and monitoring medical devices. A therapeutic medical device is configured to provide a therapy to a patient. For example, a therapeutic medical device can be configured to monitor a patient for a predetermined physiologic condition, e.g., a cardiac arrhythmia, and provide a treatment on detecting the condition. Therapeutic medical devices can include automated external defibrillators (AED), wearable cardioverter defibrillators (WCD), implantable defibrillators, or external or implanted pacing devices.

A monitoring medical device, on the other hand, is configured to sense one or more predetermined physiologic parameters of a patient, e.g., for remotely monitoring and/or diagnosing a condition of the patient. For example, such physiologic parameters may include a patient's electrocardiogram (ECG) information, heart sounds (e.g., using accelerometers or microphones), lung sounds, breath sounds, sleep related parameters (e.g., snoring, sleep apnea), tissue fluids, among others. As described in detail below, an example monitoring medical device is a cardiac monitor. A cardiac monitor may be implemented as a portable device that is carried by the patient as he or she goes about their daily routine. Such cardiac monitors can be used in mobile cardiac telemetry (MCT) and/or continuous cardiac event monitoring applications, e.g., in patient populations reporting irregular cardiac symptoms. Such patients may be prescribed a cardiac monitor for an extended period of time, e.g., 10 to 30 days, or more. In some mobile cardiac telemetry applications, a portable cardiac monitor can be configured to substantially continuously monitor the patient for a cardiac anomaly, and when such an anomaly is detected, the monitor may automatically send data to a remote server. The remote server may be located within a 24-hour manned monitoring center, where the data is interpreted by qualified, cardiac-trained reviewers and/or caregivers, and feedback provided to the patient and/or a designated caregiver. In certain cardiac event monitoring applications, the cardiac monitor is configured to allow the patient to manually press a button on the cardiac monitor to cause the device to record predetermined physiologic parameters of the patient (e.g., ECG information) for a predetermined amount of time (e.g., 1-5 minutes before and 1-5 minutes after a reported event). The cardiac monitor can be configured to monitor other physiologic parameters of the patient other than cardiac related parameters. For example, the cardiac monitor can be configured to monitor, for example, heart sounds (e.g., using accelerometers or microphones), lung sounds, breath sounds, sleep related parameters (e.g., snoring, sleep apnea), tissue fluids, among others.

In some implementations, therapeutic medical devices, as described herein, can be configured to only monitor a patient as a monitoring medical device. For example, such a therapeutic medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

In a similar manner, a monitoring medical device can have optional therapeutic elements (e.g., defibrillation and/or pacing electrodes, components, and associated circuitry) configured to operate, for example, if the monitoring medical device is reconfigured from operating in a monitoring-only mode to operating in a therapeutic mode. The optional therapeutic elements can be physically attached to the monitoring medical device as a means to convert the monitoring medical device into a therapeutic medical device for a specific use (e.g., for operating in a therapeutic mode) or patient. Alternatively, the optional therapeutic elements can be activated (e.g., by means or a physical or a software switch), essentially converting the monitoring medical device to a therapeutic medical device for a specific treatment purpose or a particular patient. Examples of medical devices including integrated monitoring and therapeutic components are described in U.S. Provisional Patent Application No. 62/258,666 filed Nov. 23, 2015, and entitled "Garments for Wearable Medical Devices," the content of which is incorporated herein in its entirety.

A physician or other caregiver in a healthcare facility can oversee the care of a number of patients. For example, the patients can be divided into multiple groups based upon what type of medical device the patient has been prescribed, as well as what specific type of treatment the patient is receiving. For example, a physician can have a group of patients that have been prescribed a monitoring medical device, and a group of patients that have been prescribed a therapeutic medical device. Within the individual groups, the patient can be further divided into additional subgroups. For example, within the group of patients that have been prescribed a medical monitoring device, a subgroup of patients can be identified that require regular evaluation (e.g., reviewing the recordings of their monitoring medical device on a daily basis). In certain implementations, within the group of patients that have been prescribed a therapeutic medical device, high risk patients that are likely to require one or more treatments during the prescription period can be identified for additional monitoring.

Throughout the course of their treatment, patients can transition from one group to another. For example, a patient can be initially prescribed a monitoring medical device. During the course of their treatment, the patient's physician can determine that the patient is likely to have, for example, an arrhythmia that would require immediate treatment. In such an example, the physician can change the patient's prescription from a monitoring medical device to a therapeutic treatment device. As noted above, changing the prescription can include activating therapeutic components contained within the monitoring medical device, attaching therapeutic components to the monitoring medical device, or replacing the monitoring medical device with a therapeutic medical device. The patient can then continue their course of treatment with the therapeutic medical device.

As patients transition between the groups and subgroups of medical devices and treatments, the imperative of continuity of care for the patient becomes critical. For example, medical personnel can remotely review the data transmitted by the medical devices either live or post-event. The reviewers can also be specialized to review only certain types of patients, thus there is risk, at the time of the transition, of loss of continuity and the new medical reviewer making ill-informed, dangerous decisions based on lack of prior patient data. Further, the types and format of patient data presented during review can vary based on the group or subgroup into which the patient is identified. Viewing the data before, during, and after the transition (of a patient between groups and subgroups) can significantly aid the medical reviewer in the diagnosis and treatment of the patient.

The systems and techniques for receiving and displaying physiological information from therapeutic and monitoring medical devices as described herein can be configured to provide a physician or other reviewer with an interface to both access patient reports for a patient prescribed a medical device (e.g., a monitoring or a therapeutic medical device) as well as to provide the reviewer with the ability to see when a patient has transitioned between devices. For example, the patient's record can be updated in real-time (or near real-time) to indicate that the patient has transitioned from a monitoring medical device to a therapeutic medical device.

For example, a patient can go to the emergency room, or another treatment facility, after exhibiting syncope symptoms. An attending physician can run a series of tests and/or scans for the patient. If the physician is unable to accurately diagnose the cause of the patient's syncope, the physician can prescribe the patient a monitoring medical device such as an MCT device. By prescribing the monitoring medical device, the physician can continue to monitor the patient without admitting the patient to the hospital. Upon prescription of the monitoring medical device, the patient can then be added to the group of patients currently prescribed a monitoring medical device for the attending physician (that prescribed the monitoring medical device) and/or the patient's primary care physician. The physician and/or another reviewer can regularly review information recorded by the monitoring medical device by accessing the patient's report (as described below in greater detail). For example, the patient's designated caregiver (e.g., the patient's physician) can be provided access to the patient's information in the form of periodic (e.g., weekly) reports. If, during review, the caregiver determines that the patient is exhibiting symptoms that are an indication that a serious cardiac arrhythmia is likely, the patient's caregiver can change the patient's prescription from the monitoring medical device to a therapeutic medical device. As noted above, such a change in prescription can include prescribing the patient a new device or activating therapeutic components in the monitoring medical device. Upon changing the prescription, the patient can be automatically moved from the group of patients prescribed a monitoring medical device to the group of patients prescribed a therapeutic medical device. As such, when accessing the patient's record, the physician or other reviewer can access the patient's record in the group of patients that have been prescribed a therapeutic medical device.

It should be noted that the example above described a patient transitioning from a monitoring medical device to a therapeutic medical device by way of example only. In some implementations, a patient previously prescribed a therapeutic treatment device can transition to a monitoring medical device. However, in both scenarios, a physician or other reviewer is provided with an interface and means to access the patient's record based upon what type of device the patient has been prescribed such that the reviewer can monitor the patient's physiological information.

For example, such physiological information can include, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels. For example, the ECG data can be associated with the patient symptom data. For example, up to a one minute or more ECG recording can be associated with one or more patient-reported symptoms as described in further detail below. For example, the physiological data may be pre-tagged by the user (e.g., the patient) prior to transmission. In an example, the patient can input one or more annotations relating to the physiological information that is then transmitted along with the physiological information.

For example, the physiological information can be obtained in the context of implanted or external medical devices for monitoring and/or providing treatment to a patient such as the therapeutic and monitoring medical devices as described above. In some implementations, the devices are capable of continuous monitoring for cardiac conditions (e.g., arrhythmias), and may only be briefly powered down, e.g., to change batteries and/or when the patient is showering or taking a bath. For example, such devices are also capable of monitoring other physiological parameters, such as, blood pressure, temperature, blood glucose levels, and blood oxygen levels. For example, such continuous monitoring can extend for periods up to 24 hours or more. In implementations, continuous monitoring can extend for long periods of time (e.g., 48 hours, one or more weeks, months, years, or more). In some implementations, the medical devices are configured to send physiological information for patients to remote sites to permit the information to be reviewed by a treating physician or other medical personnel. For example, the information can be sent pursuant to a request by the patient, the prescribing physician, or a third party. Alternatively, the information can be sent based on a medical event. In some configurations, the information can be sent periodically or according to a predetermined schedule. In some configurations, the physiological information can be sent as a substantially continuous data stream (e.g., continuous ECG monitoring data that is sent substantially in real-time), and at the same time, additional information can be sent pursuant to a request by the patient, the prescribing physician, or a third party (e.g., user-initiated event reporting along with an associated ECG strip). At the remote site, the information can be presented to a user in a variety of formats, levels of detail, and/or permission levels, in accordance with the description herein. Further, the user can generate reports from the information in any one of a variety of ways as described below.

As noted above, external medical devices as disclosed herein can include cardiac monitoring and/or therapeutic devices including, for example, automated pacing devices or defibrillators, such as in-facility continuous monitoring defibrillators (e.g., for patients that are confined to a limited space within a facility, such as, within a hospital environment, to a patient's room) or outpatient wearable defibrillators. Such devices can be configured to monitor a patient for an arrhythmia condition such as bradycardia, ventricular tachycardia (VT) or ventricular fibrillation (VF). In the case of therapeutic devices such as pacing and/or defibrillating devices, if an arrhythmia condition is detected, the device can automatically provide a pacing or defibrillation pulse or shock to treat the condition.

As noted, medical devices as disclosed herein can include wearable cardiac monitors and/or defibrillators (which can include pacing functionality). In some examples, medical devices as disclosed herein can include implanted medical devices (e.g., implantable defibrillators or pacing devices). Devices described herein as non-invasive can be contrasted with invasive medical devices, such as implantable defibrillators or implantable pacing devices.

Other example external devices capable of interacting with the information displaying systems and methods disclosed herein and/or techniques described herein include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the automated defibrillators described herein can be pacing-enabled, e.g., capable of providing therapeutic pacing pulses to the patient. In an example, the external medical devices as described herein can be ambulatory, e.g., the device is capable of and designed for moving with the patient.

Example Therapeutic Medical Device:

FIG. 1 illustrates an example therapeutic medical device that is external, ambulatory, and wearable by a patient 9, and configured to implement one or more configurations described herein. For example, the medical device 1 can be a non-invasive medical device configured to be located substantially external to the patient. Such a device can be, for example, an ambulatory medical device that is capable of and designed for moving with the patient as the patient goes about his or her daily routine. For example, the therapeutic medical device, shown in FIG. 1 as a wearable defibrillator 1, as described herein can be bodily-attached to the patient such as the LifeVest® wearable cardioverter defibrillator available from ZOLL® Medical Corporation of Pittsburgh, Pa. and Chelmsford, Mass. The wearable defibrillator 1 can be worn by a patient 9 and can include a garment 2 (shown in phantom in FIG. 1), an electrode assembly 3, and a monitor 5 operatively connected to the electrode assembly 3. The garment 2 can be configured as a harness, shirt, or other apparel and is configured to permit the defibrillator 1 to be worn on about the torso of the patient 9. The electrode assembly 3 can be configured to be assembled within the garment 2.

Such wearable defibrillators can be typically worn nearly continuously for two to three months at a time. During the period of time in which they are worn by the patient, the wearable defibrillator 1 can be configured to continuously monitor the vital signs of the patient, to be user-friendly and accessible, to be as light-weight, comfortable, and portable as possible, and to be capable of delivering one or more life-saving therapeutic shocks when needed. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944, the content of each of which is incorporated by reference in its entirety.

With continued reference to FIG. 1, the electrode assembly 3 can include a plurality of sensing electrodes, such as sensing electrodes 7a, 7b, 7c, 7d, which can be configured to contact a patient 9 when the wearable defibrillator 1 is worn by the patient 9. According to one example, the sensing electrodes 7a, 7b, 7c, 7d can be configured to receive ECG signals from the patient 9. For instance, the sensing electrodes 7a, 7b, 7c, 7d can be positioned on the patient 9 to receive ECG signals from a front-to-back channel and from a side-to-side channel. For example, the front-to-back (FB) channel can include one of sensing electrodes 7a, 7b, 7c, 7d positioned on the chest of the patient 9 and another one of the sensing electrodes 7a, 7b, 7c, 7d positioned on the back of the patient 9. For example, the side-to-side (SS) channel can include one of the sensing electrodes 7a, 7b, 7c, 7d positioned on the left side of the chest and another one of the sensing electrodes 7a, 7b, 7c, 7d positioned on the right side of the chest of the patient 9. In some examples, the sensing electrodes 7a, 7b, 7c, 7d can be operatively connected to a distribution node 11 of the electrode assembly 3.

In some implementations, the electrode assembly 3 can also comprise therapy electrodes 13a, 13b, 13c operatively connected to the distribution node 11. The therapy electrodes 13a, 13b, 13c can be configured to deliver one or more life-saving therapeutic shocks when needed. In some examples, the electrode assembly 3 can also include other sensing electrodes and devices (not shown) such as, but not limited to, heart beat sensors, accelerometers, and sensors capable of measuring blood pressure, heart rate, thoracic impedance, respiration rate, heart sounds, acoustic sensors, audio transducers, and the activity level of the subject. The monitor 5 can be operatively connected to one or more of the therapy pads 13a, 13b, 13c and sensing electrodes 7a, 7b, 7c, 7d via a trunk cable or any other suitable cable or connection device. Wiring or other connection devices can be used to connect at least one portion of the distribution node 11 to the sensing electrodes 7a, 7b, 7c, 7d and therapy electrodes 13a, 13b, 13c. The monitor 5 can include communications circuitry for sending data, such as patient physiological information, from the wearable device 1 to a remote site, such as a remote network, server, or electronic device.

In implementations, an example therapeutic medical device can include an in-hospital continuous monitoring defibrillator and/or pacing device, for example, an in-hospital wearable defibrillator. In such an example, the electrode assembly (e.g., similar to the electrode assembly 3 described above) can be adhesively attached to the patient's skin. For example, the electrode assembly can include disposable adhesive electrodes. For example, the electrode assembly can include sensing and therapy components disposed on separate sensing and therapy electrode adhesive patches. In some implementations, both sensing and therapy components can be integrated and disposed on a same electrode adhesive patch that is then attached to the patient. The electrode assembly can be positioned on the patient in a similar manner as described above. In an example implementation, the electrode assembly can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device may be confined to a hospital bed or room for a significant amount of time (e.g., up to 90% of the patient's stay). As a result, the monitor 5 user interface can be configured to interact with a user other than the patient, e.g., a nurse, for device-related functions such as initial device baselining, setting and adjusting patient parameters, and changing the device batteries.

In implementations, an example therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly (e.g., similar to the electrode assembly 3 described above) can be adhesively attached to the patient's skin and have a similar configuration as the in-hospital defibrillator described above.

For example, the therapeutic medical devices described above (e.g., the wearable defibrillator, the in-hospital defibrillator, and the short-term defibrillator) can protect patients at risk for sudden cardiac death. It can be used for a wide range of patient conditions or situations, including following a recent myocardial infarction or coronary revascularization. In one scenario, the wearable defibrillator can give caregivers time to optimize medical therapy and assess a patient's long-term risk for sudden death. The wearable defibrillator is configured to continuously monitor the patient's heart and, if a life-threatening heart rhythm is detected, the device can issue an alert to the patient. For example, the monitor 5 can include a touchscreen for programming as well as patient interaction, and response buttons for the patient to use when responding to treatment alerts. If the patient does not respond (e.g., by holding down the response buttons) the wearable defibrillator can deliver a treatment shock to restore normal heart rhythm.

Figure 2A:
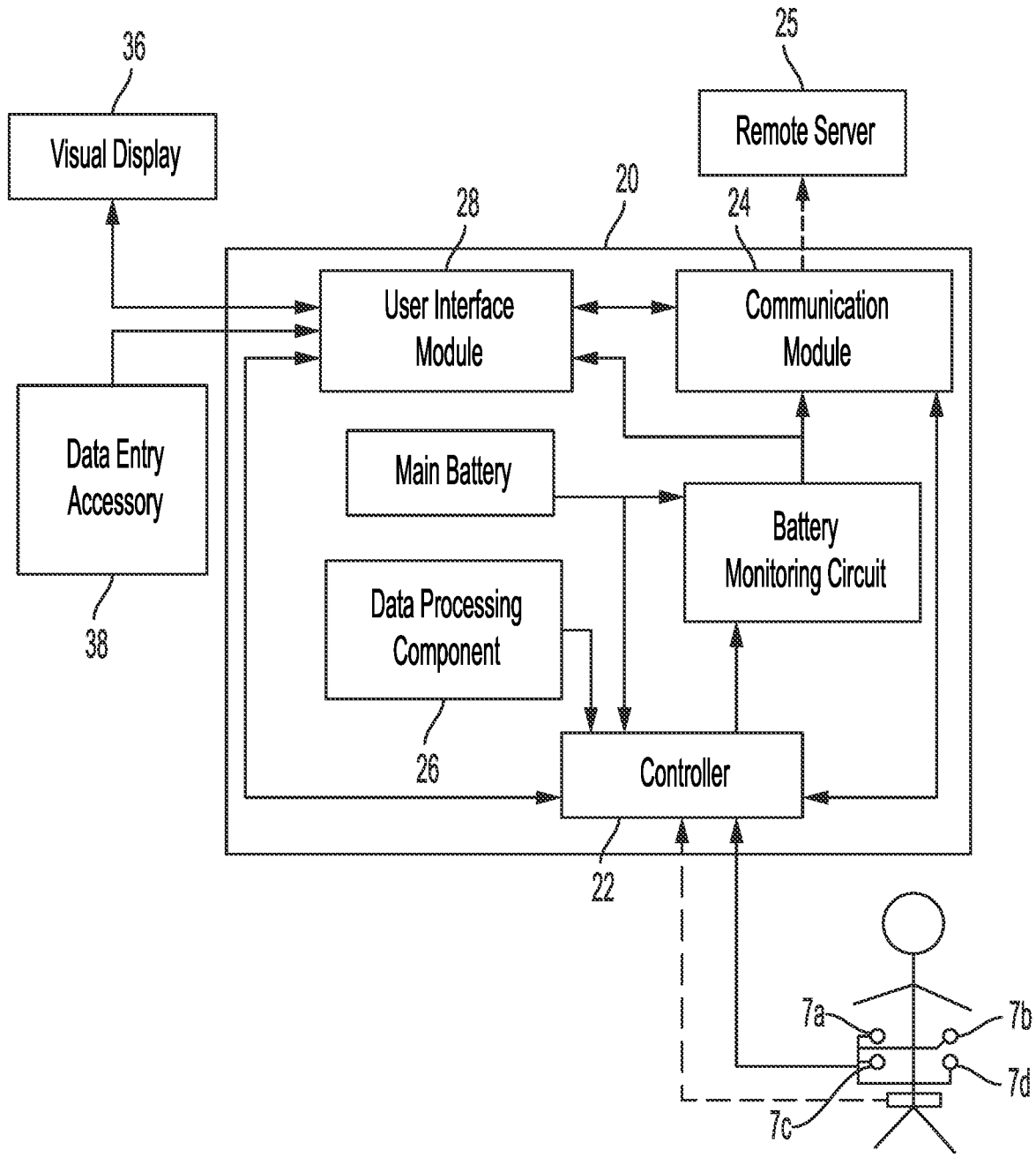
FIG. 2A depicts a block diagram illustrating various functional components of an example monitoring medical device (e.g., a cardiac or patient monitor), in accordance with an example of the present disclosure.

Example Monitoring Medical Device:

With reference to FIG. 2A, a monitoring medical device, for example, a cardiac or patient monitor 20, is illustrated. The monitor 20 can include a controller 22 that is communicatively coupled (e.g., wired or wirelessly coupled) to receive from sensors and/or electrodes 7a-7d appropriately positioned on patient 9 signals (e.g., ECG data and/or heart sounds data from an acoustic sensor) indicative of cardiac activity of patient 9. In some examples, the sensors and/or electrodes can be an integral part of the housing structure of the patient monitor.

In some examples, the patient monitor 20 can be a cardiac monitor configured to receive cardiac data (e.g., ECG data and/or heart sounds data from an acoustic sensor). In some examples, the patient monitor 20 can, in addition to cardiac monitoring, perform monitoring of other relevant patient parameters, e.g., weight, glucose levels, blood oxygen levels, and blood pressure. The patient monitor 20 can also include a physiological data processing component 26 for collecting and conditioning the physiological data prior to storing the data locally at computer-readable storage media on the monitor 20 itself and/or transmitting the data to a remote server 25 or device.

In some examples, the patient monitor 20 can include motion sensors to track patient movement. In some examples, the patient monitor 20 can be a handheld device, such as a smartphone, a personal digital assistant, or a tablet device, comprising an application capable of receiving and/or processing patient data, either from internal sensors (e.g. motion sensors) or external sensors (e.g. wireless or wired sensors capable of sensing patient parameters, e.g. ECG, heart sounds, weight, glucose levels, blood oxygen levels, and blood pressure).

In some examples, the patient monitor 20 includes a user interface module 28 that allows the patient to perform one or more of the following activities: to control aspects of operation of the device, to manually enter patient information (e.g., patient name, age, gender), to manually enter information about a patient condition, and to initiate sending information to the remote server 25. The user interface module 28 can include a visual display 36 and a data entry accessory 38, such as buttons, trackballs, touchpads, and the like, for manually entering selections in response to a prompt from the user interface module 28. In other examples, the user interface module 28 can include a touch screen display for displaying information to the user and for receiving input (e.g., selections) from the user.

The patient monitor 20 also includes communication circuitry, referred to as communications module 24, for communicating with the remote server 25 (e.g., one or more computer systems) over a communications network. The patient monitor 20 can also communicate with other devices which may be a remote handheld device (e.g., a smartphone, a personal digital assistant, or a tablet device).

In some examples, the patient monitor 20 can periodically (e.g., on a preset schedule) establish a wireless communication (e.g., cellular communication, WiFi or Bluetooth) and send data, such as patient physiological information, to the server over the network. For example, such physiological information can include, without limitation, patient symptom data (e.g., patient-reported symptoms and/or automatically detected patient information), related cardiac data including premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels.

In other examples, the patient monitor 20 can be configured to aperiodically establish communication with the remote server 25 for the purpose of sending patient data. For example, the physiological data can be processed in accordance to a predetermined standard for transmission and can be transmitted in a secure HIPAA-compliant manner.

In other examples, the patient monitor 20 can be configured to send information to the remote server 25 when a transmission is initiated by the patient. For example, the patient can indicate that he or she is experiencing a symptom. As discussed hereinafter, the patient monitor 20 can be configured to send physiological information for the time period when the symptom was experienced to the remote server 25.

Figure 2B:
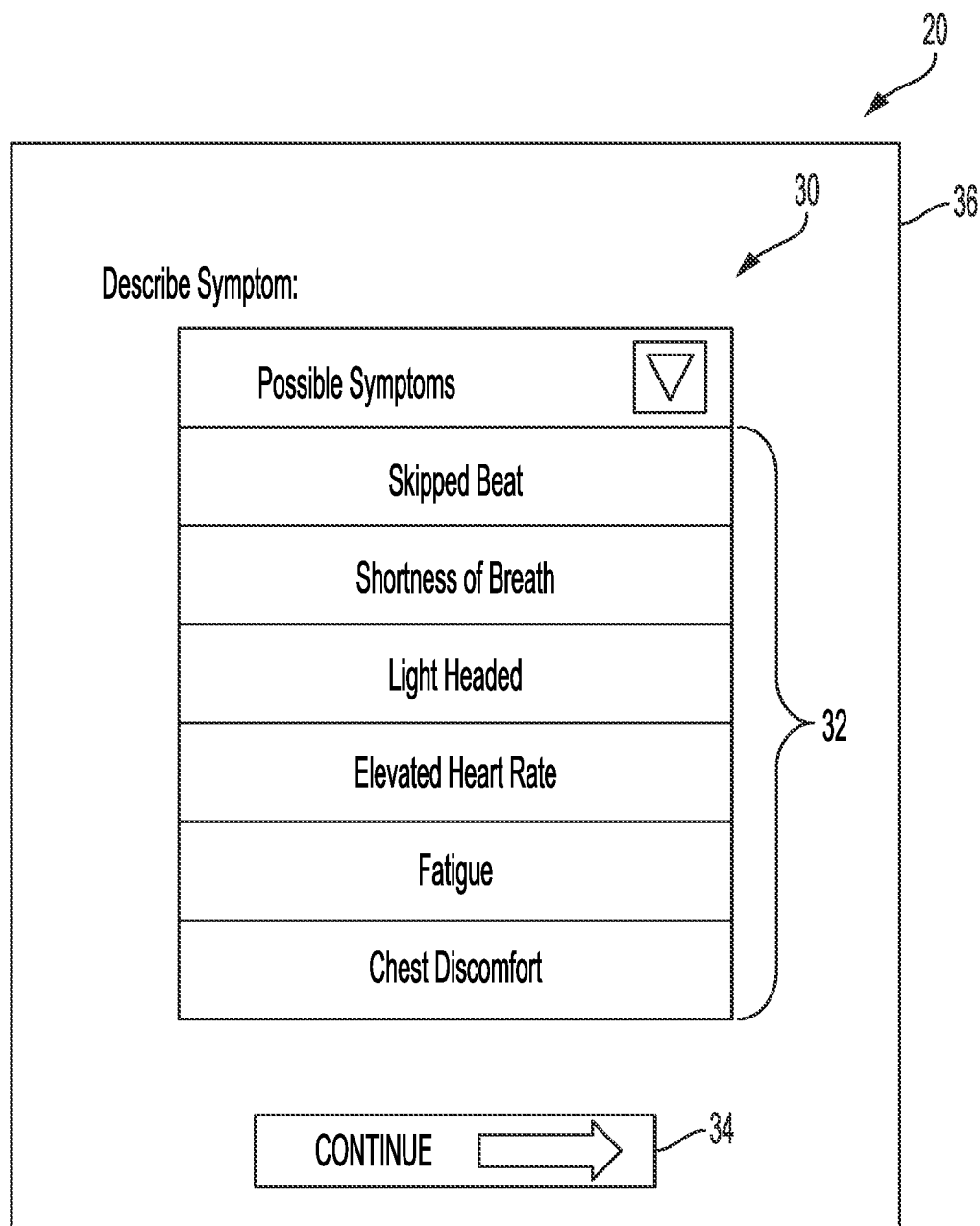
FIG. 2B depicts a schematic drawing of an example screen capture for the monitoring medical device of FIG. 2A, in accordance with an example of the present disclosure.
Figure 2C:
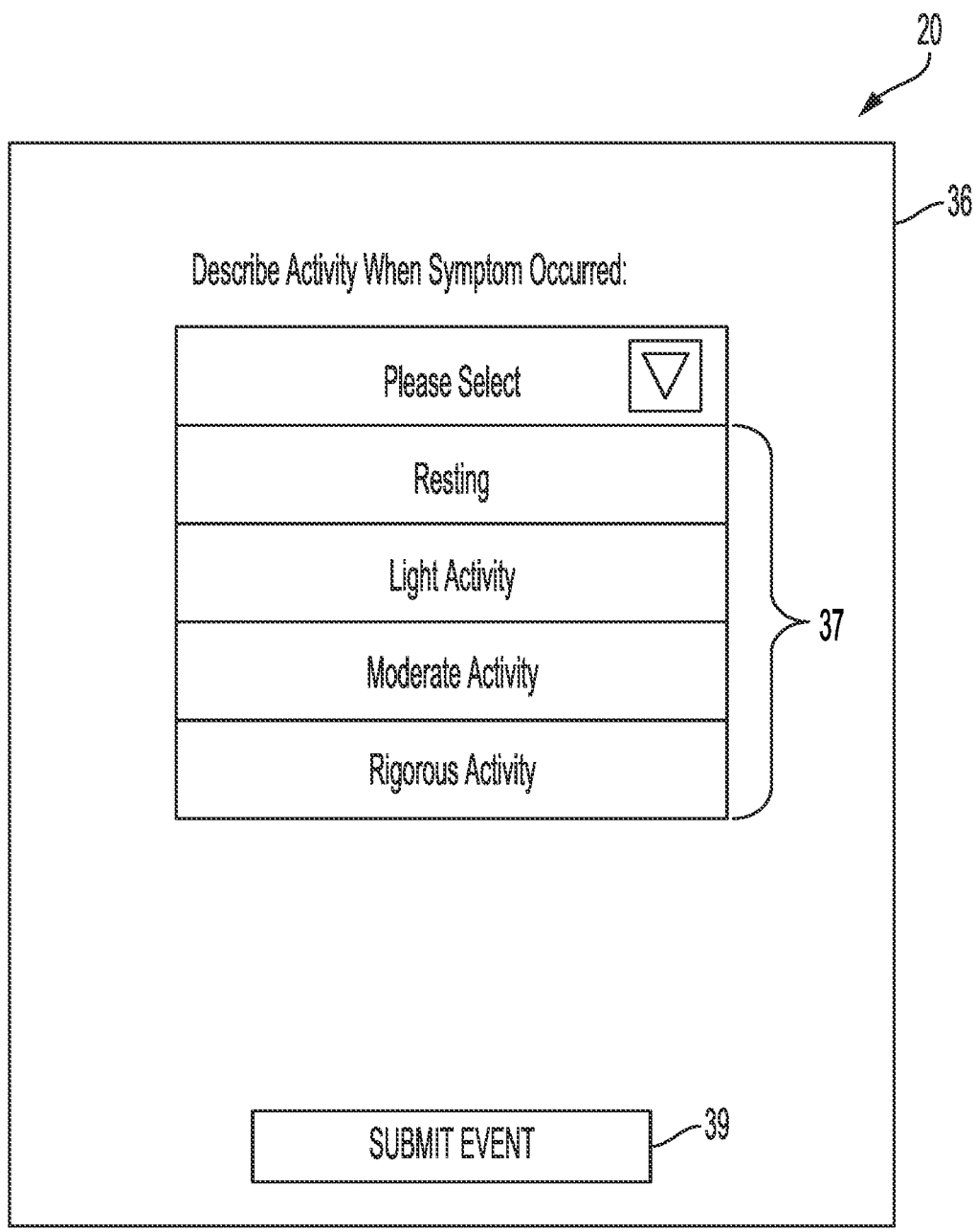
FIG. 2C depicts a schematic drawing of an example screen capture for the monitoring medical device of FIG. 2A, in accordance with an example of the present disclosure.

With reference to FIGS. 2B and 2C, an exemplary series of screens that can be shown on the visual display 36 of the user interface module 28 are illustrated, which allow the patient to identify and submit patient symptom information. As shown in FIG. 2B, the visual display 36 can provide a patient with an interactive drop down menu 30 or check list that includes one or more user-selectable portions for the patient to select a particular symptom from a list 32 of options. Options for patient systems can include one or more of: feeling a skipped beat, shortness of breath, light headedness, racing heart rate, fatigue, fainting, chest discomfort, weakness, dizziness, and/or giddiness. Once the patient symptom is selected, the user can select a "Continue" button 34 to advance to a second data entry screen. At the second screen, as shown in FIG. 2C, the visual display 36 can provide a prompt to the patient asking the patient to identify his or her level of physical activity when the symptom was experienced. The patient can select a level of activity from a list 37 including one or more options, such as resting, light activity, moderate activity, or rigorous activity. Once the activity level is selected, the user can initiate a data transmission from the monitor 20 to the remote server and including relevant physiological information by, for example, selecting a "Submit" button 39.

In the context of a patient-initiated data transmission, for example, in response to the selection by the patient, the patient monitor 20 can capture a portion of the physiological signal for a period of time when the symptom was experienced (e.g., in the case of an ECG signal, such a portion can be in the form of an ECG strip). The patient monitor 20 can establish communication with the network, and send the captured portion of physiological information to the remote server 25. For example, a captured ECG stream can be a strip of about less than a minute. For example, a captured ECG strip that is associated with the symptom information can have a duration of approximately one minute. In some cases, the ECG strip can have a duration that is appropriate for the symptom(s) reported by the patient and/or event detected by the patient monitor 20. In some situations, it may be appropriate for the ECG strip recording to be of a duration lasting up to an hour (e.g., in the event of a recorded atrial flutter).

In some implementations, the patient monitor 20 can continuously record ECG data, and, at the same time, also record an ECG strip relating to one or more events of interest (e.g., patient-reported symptoms). As such, if a physician wishes to view ECG data for a period of time prior to or after the recorded ECG strip relating to an event of interest, such data is available for review from the continuously recorded ECG data stream.

With reference again to FIG. 2A, in some examples, the physiological data processing component 26 can be configured to analyze physiological information recorded by the monitor to identify when an event occurs. A non-limiting list of possible events that can be identified by analysis performed by the data processing component 26 of the patient monitor 20 includes: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. The data processing component 26 can identify the event by performing an analysis algorithm, as is known in the art, for analyzing the patient physiological information. For example, to identify atrial fibrillation, the monitor 20 can be configured to analyze a measured ECG signal and determine an average QR interval for a plurality of preceding beats. The average QR interval or a change in the QR interval can be analyzed to identify atrial fibrillation events. Other analysis can be performed on an ECG signal to identify other events or conditions. In some examples, the events can be device-related events, such as when the device detects a battery-related condition, e.g., battery needs to be replaced, excessive noise, potential misidentification of one or more physiological parameters, or if one or more self-test features in the device fails or needs attention. When a physiological event or condition is identified, the patient monitor 20 can capture the physiological information related to the event, establish communication with the network, and send physiological information related to the event to the remote server. Similarly, when a device-related event or condition is identified, the patient monitor 20 can send diagnostic information relating to the event and/or condition. In some cases, where the device-related event relates to a noise event or a possible misidentification of physiological parameters, the patient monitor 20 can be configured to also send physiological information collected during the period of the device-related event for further analysis. Such types of transmission can be considered event based data transmission.

In another example, the patient monitor 20 can send all recorded physiological information to the remote server. The remote server 25 can manually or automatically perform the analysis for the events. For example, the patient monitor 20 can send data in batches at periodic intervals, such as once an hour or once a day, to the remote server 25 over the communications network.

In another example, the monitor 20 may continually communicate patient physiological information in substantially real-time to the remote server 25 whenever connectivity to the network is present. For example, continuous data transfer of physiological information can occur substantially in real-time, and may have brief device-induced delays, such as delays introduced through electronic switching. In some examples, the monitor 20 can communicate patient physiological information with a user-configurable delay between the time the information is recorded, and sent and/or delivered to the remote server.

Figure 3:
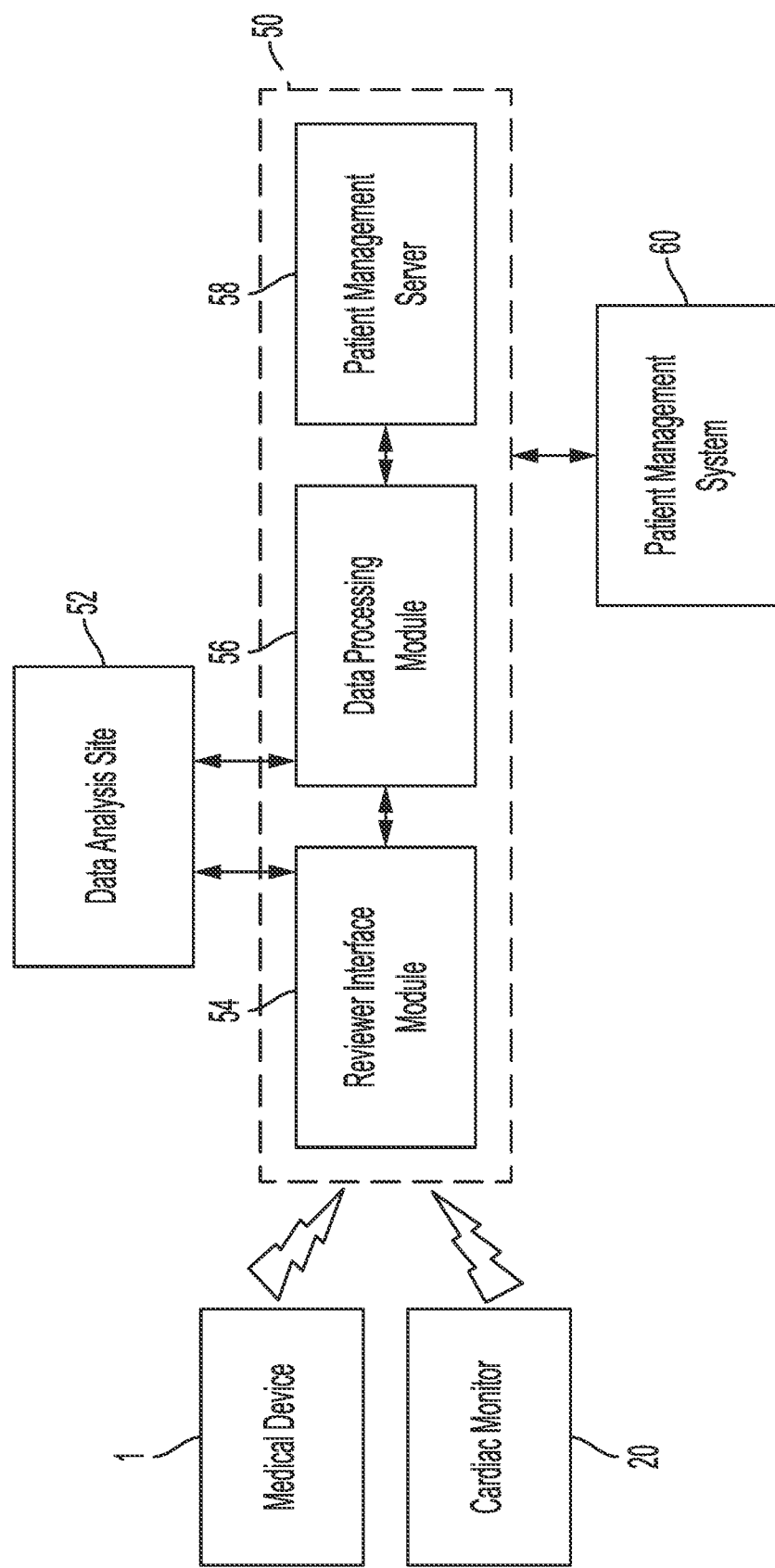
FIG. 3 depicts a schematic drawing of an example mobile cardiac telemetry system including a communications network, in accordance with an example of the present disclosure.

Communications Network:

With reference to FIG. 3, a communications network 50 for sending physiological information from the therapeutic medical device (e.g., wearable defibrillator 1) and the monitoring medical device (e.g., cardiac monitoring device 20) to one or more remote locations for analysis and/or review is illustrated. For example, the communications network 50 can include a reviewer interface module 54, a data processing module 56, and a patient management server 58. It should be noted that the reviewer interface module 54, the data processing module 56, and patient management server 58 can interface in any manner with the medical devices and/or the data analysis site. For example, data from the medical devices can first be processed by the data processing module 56 (e.g., as described below, certain analysis can be carried out on the incoming physiological data) and then passed along to the reviewer interface module 54 for further analysis and interpretation in accordance with the disclosure herein. Conversely, data can be reviewed by a reviewer via the reviewer interface module 54 before being processed in the data processing module 56, e.g., reviewer-edited ECG strips from the reviewer interface module 54 can be automatically annotated with pertinent information (e.g., patient information and/or interpretation tools) and sent to the patient management server 58.

In some configurations, the data processing module 56 can operate independently of the reviewer interface module 54. For example, the data processing module 56 can analyze data from one type of device, e.g., the therapeutic medical device (such as wearable defibrillator 1), and send any analysis, data, and/or reports to the patient management server 58.

The communications network 50 can include a wired network, a long range wireless network (WiFi), a short-range wireless network (BLUETOOTH®), a cellular network, and/or combinations thereof for transmitting data from the medical devices 1, 20, between the modules 54, 56, 58, and to the patient management system 60. As described above, the medical devices 1, 20 can send information over the communications network 50 either substantially continuously or on a preset schedule, based on a request by the patient, automatically based on identification of an event on the device, and/or based on a request from a remote party such as a treating physician.

In an implementation, the following process can be used for uploading data from the cardiac monitor (e.g. medical devices 1, 20) to a server at a remote location (e.g., the communications network 50 and/or the patient management server 58). For example, the cardiac monitor 20 can perform an HTTP POST to upload the data, e.g., in the form of one or more electronic files. The cardiac monitor 20 can upload the files into event directories on the patient management server 58, e.g., categorized by a type of the file such as "event," "ECG," and/or "Report." One or more file parsing functions can be called to parse the files for extracting and storing the data in one or more tables in a database on the patient management server 58. For example, events data can be stored in an events table within a database located on the patient management server 58. In a similar manner, ECG data can be stored within an ECG table, data collected from other types of sensors, detector, or monitors, can be stored in other appropriate tables, and reported, analyzed, or processed data, that includes events identified by processing algorithms, can be stored in respective reports tables.

Reviewer Interface Module 54:

With continued reference to FIG. 3, the reviewer interface module 54 can be configured to receive information from the medical devices 1, 20 and, in some examples, to transmit the received physiological information to a data analysis site 52 for review by a technician or reviewer. At the data analysis site 52 (e.g., a mobile telemetry center or system) the patient physiological information collected by the medical devices 1, 20 is manually reviewed by the technician or reviewer and analyzed for the purpose of identifying and/or confirming any of a number of patient conditions and/or events. For example, events that can be reviewed by the reviewer can include one or more of the following: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations.

The data analysis site 52 can be implemented as an end user terminal operably attached to a remote server or directly connected to, for example, the reviewer interface module 54 and the data processing module 56. For example, the data analysis site 52 can be located at a manufacturer of medical devices, or at a data analysis vendor or other similar vendor contracted by or otherwise associated with the device manufacturer.

In some examples, the reviewer can access the reviewer interface module 54 through an end user terminal that can include, but is not limited to, any one of a: workstation, desktop computer, tablet, smartphone, and/or personal digital assistant. Based upon the desired functionality of the end user terminal, the terminal can include, for example, multiple displays such that the reviewer can run multiple applications for viewing reports related to distinct medical devices. Similarly, the end user terminal can be configured to run multiple instances of the same application, each instance accessing information or reports related to a different medical device. For example, a reviewer can launch a first instance of the application to view reports related to patients that have been prescribed a therapeutic medical device and launch a second instance of the application to view reports related to patients that have been prescribed a monitoring medical device. The reviewer can launch the first and second instances of the applications during a single reviewing session, thereby providing the reviewer with the option of switching between the instances to view the two groups of patients, i.e., a first group including patients prescribed a therapeutic device and a second group including patients prescribed a monitoring medical device. In certain implementations, the end user terminal can be configured to open multiple instances upon opening the application such that the reviewer has access to all groups of patients. In some examples, the end user terminal can be configured to launch a single instance in response to a user selection of which group of patients to access. Upon selecting another group to review, the end user terminal can be configured to launch another instance of the application.

In certain implementations, the reviewer can review all the information transmitted by a medical device 1, 20 or monitor during a cardiac monitoring study. For example, the reviewer can use the reviewed data to generate reports that are then sent to the patient management system 60. For example, the reviewer interface may include one or more of patient and/or event information, display tools, editing tools, and ECG graphs and related tools.

The technician or reviewer prepares a patient report based on the obtained physiological information. In preparing the report, the technician or reviewer can, for example, manipulate relevant portions of the physiological information to make relevant portions of physiological information easier for the end user to identify and review. The technician or reviewer can also edit portions of data, such as segments of an ECG signal, and provide annotations about which portions of the ECG show different types of events. The report can also include other patient information and/or statistics determined from the total monitoring period (e.g. percentage of time in a particular cardiac condition, total patient wear time, etc.). Other statistics or metrics that can be included in the patient report can include, for example, percentage of time in atrial fibrillation, percentage of time with bradycardia, percentage of time with tachycardia, average heart rate, most common symptom reported by the patient, number of identified events, and a number of treatments by a therapeutic medical device.

In an example, the technician or reviewer can prepare the patient report in the following manner. At the data analysis site 52, a work queue can be populated based on the received medical device date (e.g., data from a plurality of cardiac monitors), each assigned to a different patient. For example, the reviewer may use the work queue to prioritize and/or sort through work items for review. The reviewer may log into a user account at the data analysis site 52, and may be able to customize an appearance of the interface for reviewing the work items. In some examples, the reviewer may be able to perform a search for a patient of interest, event or record of interest, a name of the reviewer assigned to handle the work item, or any of the other available data fields. For example, the work queue may present information under one or more of the following headers: a device serial number, patient identification, patient name, patient date of birth, data and time for the record, a number of events within the record, a status of the record (e.g., under review, un-reviewed, or reviewed), and a name of the reviewer assigned to handle the record. For example, the assigned field can also list information regarding the patient's caregiver and/or other prescriber information. In some examples, one or more order details that can be associated with the patient and/or the monitoring device, such as, a phone number, a gender of the patient, whether or not the patient has a pacemaker, implantable defibrillator, an entry indicating a duration of need for the monitoring device, and an indication or patient history of bradycardia and/or tachycardia.

In some examples, the reviewer can also review patient/event information including patient data and/or event descriptions. For example, an event description can include a type of event (e.g., atrial fibrillation onset, atrial fibrillation offset, tachycardia onset, tachycardia offset, bradycardia onset, bradycardia offset, a pause in the monitoring, a manually patient-initiated event, and a doctor-requested event, such as when a caregiver requests the patient to perform an action, or where the event is remotely triggered on by or on behalf of the caregiver). In an implementation, the event that the medical device 1, 20 detected can be automatically displayed to the reviewer as the default. If the reviewer, on reviewing the event, decides the detected event is incorrect or not an event, he or she can select the correct type event from, e.g., a drop-down list. When a new event is selected, in some examples, a confirmation pop-up screen can be displayed. After change is confirmed, the current event type can be crossed out and the new type displayed. In this manner, when a report is generated, the physician can see the original event, and the reviewer's changes and any explanations, if necessary.

In some implementations, symptom information can be collected and displayed as described herein. In the case of a patient-indicated event, as discussed above in connection with the patient monitoring devices, the patient may select a symptom to go with the ECG recording. Similarly, in the case of a patient-indicated event, the patient may select an activity level (e.g., resting, light, moderate, or rigorous activity) to go with the ECG recording. The patient selections can be displayed to the reviewer and, optionally, can be included in notes or annotations associated with other portions of the patient report.

Based on the reviewed information, the reviewer prepares the one or more patient reports to be forwarded to the end user. In some examples, one or more editing and viewing tools can be provided to aid the reviewer in editing the ECG and viewing the ECG from different views (e.g., by applying one or more filters and/or changing a speed or amplitude). For example, default values can be set for the views and ECG parameters. For example, the default speed for ECG review can be 25 mm/s. For example, the default amplitude can be 1 mv/10 mm. For example, a filtering function can include options such as low pass (50 Hz), high pass (0.5 Hz), or Notch (60 Hz). In this manner, the ECG reviewer may be able to view obscured points on the ECG. Other tool/features include, an ability to invert trace on the ECG strip, toggle the ECG grid, and/or reset the views to the default values. With respect to editing tools, the reviewer may be able to mask (partially or completely obscure a section of ECG without removing it completely, for example, to indicate that the section has noise or otherwise should not be considered for review), label the R beats between reference points, automatically guide points to the closest R peaks on the graph, perform a manual measurement of a single-beat heart rate, measure a PR interval, measure a QRS complex, and/or measure a QT interval. The reviewer may be able to view any single one or combination of three ECG leads. For example, the lead can be labeled Lead 1, Lead II, and Lead III. Once a report is completed, the data analysis site 52 and/or reviewer interface module 54 can transmit the report to the patient management server 58 and/or to the patient management system 60 for review by the end user.

Data Processing Module 56:

Physiological information from the medical devices 1, 20 can also be transmitted directly or indirectly to the data processing module 56. In some examples, the data processing module 56 can be configured to automatically analyze the physiological information, such as portions of an ECG signal, using algorithms that provide an indication of patient status and/or cardiac function. For example, a non-limiting list of statistics that can be calculated based on a measured ECG signal include: premature ventricular contraction (PVC) count, heart rate information, heart sounds data, ECG data (e.g., continuous ECG data), lung fluid measurements/data, patient thoracic impedance measurements/data, pectoral impedance measurements/data, blood pressure, temperature, blood glucose levels, and blood oxygen levels. The calculated statistics can be included in a separate automatically generated patient report. Alternatively, statistics calculated by the data processing module 56 can be forwarded to the reviewer or reviewer interface module 54 and can be combined with the manually prepared patient report. The reviewer can also use the statistics during his or her review of the acquired physiological data.

In some examples, the data processing module 56 can be configured to apply predictive algorithms to the measured physiological information to provide an estimation or prediction for occurrence of a potential medical event for a subject within an associated period of time. The estimation or prediction can be provided in the form of a risk score which can be based on, for example, physiological measurements extracted from the ECG signal including heart rate variability, PVC burden or counts, activity, noise quantifications, atrial fibrillation, momentary pauses, heart rate turbulence, QRS height, QRS width, changes in the size or shape of the morphology, cosine R-T, artificial pacing, corrected QT interval, QT variability, T wave width, T wave alternans, T-wave variability, ST segment changes, early repolarization, late potentials, fractionated QRS, or fractionated T wave content. The risk score can indicate, for example, that a patient condition is generally improving, worsening, or remaining stable. Further, risk score values can be used to determine an appropriate course of treatment or, for example, to determine or suggest whether a patient should be admitted or, if already admitted, should remain in a hospital.

Patient Management Server 58:

Once the report is prepared by the reviewer or automatically created at the data processing module 56, it can be sent to the patient management server 58 for processing and can be accessed by the end user through the patient management system 60. In some examples, data from the medical devices can be routed to the patient management server 58 with minimal or no processing at either the reviewer interface module 54 or the data processing module 56.

For convenience, the information or document provided to the end user is referred to herein as a patient report. However, it is understood that, in some examples, data and/or physiological information can be sent directly from the medical devices 1, 20 to the patient management server 58 without being analyzed, edited, or modified at modules 54, 56. Thus, in some examples, raw or un-analyzed physiological data can be provided to the patient management system 60. In other examples, the measured physiological information can undergo limited filtering or processing to improve readability or clarity, but further analysis of the measured data is performed at the patient management system 60 either automatically or manually by the user. In still other examples, the patient report can only include a particular subset of physiological information that would be of interest to the end user. In still other examples, the report can include only analysis, such as a percentage of time in atrial fibrillation, and no actual physiological data as collected by the medical device.

Patient Reports:

Patient reports can include various elements and/or information fields based on the needs and/or preferences of a particular end user. Examples of common report elements include one or more of: dates of service (e.g., the period for which the device was ordered to be worn), date/time within the wear period to which the report refers (applies to daily reports, event reports, and physician requested reports), patient identifying data (e.g., patient name, sex/gender, date of birth, and/or phone number, if any), prescribing physician information (e.g., physician's name, office contact information, a reason for prescription, and, if available, one or more medical order code(s), and/or any description of "symptoms" provided by the physician in the order).

In some examples, the patient report can include technician's notes, e.g., any general notes that the technician makes when reviewing the event in question. The report can also include ordering physician's notes. For example, it may also include a signature line and date line for the physician. The physician may be able to fill in these elements electronically (e.g. through the delivered .pdf or via a web interface prior to report generation and delivery). For each event captured during the report period, the ECG strip associated with all events taking place during the reporting period can be included in the report.

In some examples, the physician (or other reviewer of the patient report) can be, in a report based on the recorded ECG data received from the patient monitor 20, provided with a few seconds (e.g., fewer than 5-10 seconds) of ECG data relating to an ECG strip of interest. In an implementation, the physician can be provided a few seconds (e.g., fewer than 5-10 seconds) of data at the beginning or an end of the recorded ECG strip. For example, the physician can be provided 1-2 seconds of an ECG strip indicating atrial flutter, which, in some situations could last for an hour or more. As discussed hereinafter in connection with the patient management system 60, the physician may customize the amount of information he or she would like to view based on the cardiac condition, e.g., a cardiac arrhythmia condition such as ventricular tachycardia or ventricular fibrillation. For example, the physician can set within his or her user profile (associated with a user account on the system) certain preferences regarding the ECG data and may customize one or more reporting parameters associated with the data. As an example, the physician can indicate that he or she prefers only the first 10 seconds of an ECG strip associated with some or all of events of interest. If the physician later wishes to view more ECG strip data, he or she can cause the system to display the additional information. For example, the request for the additional ECG strip data can be manually processed by a technician and/or a reviewer. In some cases, the request for additional ECG strip data can be automatically processed by the system based on, for example, the physician's preset preferences or the physician's associated level of data access (e.g., based upon a determination that the physician has applicable security credentials associated with their account to access the additional data).

With continued reference to FIG. 3, as previously discussed, the patient reports can be provided to the patient management system 60 either periodically or at aperiodic intervals, such as in response to a particular event or action by the patient, treating physician, or another interested party. For example, reports can be generated and provided to the patient management system 60 in response to a specific event (as opposed to being generated on a regularly-occurring basis or the end of device use), and delivered to the reviewing physician. In some examples, one or more triggering events can be as follows: Atrial Fibrillation, Tachycardia, Bradycardia, Pause, Patient-initiated, and Baseline.

In some examples, physicians are able to request reports corresponding to a specific time frame during device use. The time frame of these reports may or may not correspond to a manual or automatically triggered event.

In some examples, for each day of cardiac monitoring use, a summary report can be compiled and delivered to the physician including information on automatic and patient-triggered cardiac events as well as daily ECG metrics.

In some examples, end of use reports can be compiled upon completion of a cardiac monitoring service, summarizing cardiac event findings and ECG trending metrics over the entire wear period. Such reports can summarize all findings during the report period (e.g., throughout wear time).

As discussed herein, the patient management system 60 is configured to receive patient reports for different patients and to allow the end user to view the reports based on various selecting criteria or other factors. For example, the patient management system 60 can be configured to receive patient reports from different types of monitoring devices, from patients suffering from a variety of different physiological conditions, and/or for patients associated with different locations or hospitals. The patient management system 60 allows the end user to select which types of reports are viewed at a particular time.

Patient Management System:

Having described the therapeutic and monitoring medical devices 1, 20 and communications network 50, the patient management system 60 will now be discussed in detail. As discussed above, the patient management system 60 allows a reviewer, such as a prescribing physician, a caregiver, or his/her office staff, to control the order and contents of patient reports to review. For example, as discussed herein, the reviewer can select to review information from a particular class of medical devices (e.g., a therapeutic device or a monitoring device), can display only reports generated based on particular patient symptoms or events, and/or can customize the order or types of data presented.

The patient management system 60 can be implemented as an end user terminal operably attached to a remote server such as patient management server 58 as shown in FIG. 3. In some implementations, the patient management system can be an end user terminal configured to access a first server (e.g., in a hospital or physician's office) to establish a local area network connection. The first server can be configured to operably connect to the remote server such as patient management server 58 as shown in FIG. 3.

The end user terminal can be a computing device implemented as, for example, a desktop workstation, a laptop computer, a mobile device such as a smartphone or tablet computing device, and/or other similar computing devices. Based upon the desired functionality of the end user terminal, the terminal can include, for example, multiple displays such that the reviewer can run multiple applications for viewing reports related to distinct medical devices. Similarly, the end user terminal can be configured to run multiple instances of the same application, each of the instances accessing information or reports related to a different medical device. These examples are discussed in greater detail with respect to FIGS. 4A and 4B.

In certain implementations, the patient management system 60 can include multiple software modules or applications that are independently configured to access data related to different medical devices from, for example, a common or shared databased stored on the patient management server 58. For example, the patient management system 60 can include a wearable defibrillation report application that can be configured to access the patient management server 58 and obtain patient reports (or portions of patient reports) related to patients currently prescribed wearable defibrillators. Similarly, the patient management system 60 can include a cardiac monitor report application that can be configured to access the patient management server 58 and obtain patient reports (or portions of patient reports) related to patients currently prescribed cardiac monitors. Such an arrangement provides for a clear separation of device-specific information and can provide a person reviewing the patient reports (e.g., an attending physician) with a mechanism to quickly filter the data included in the patient reports based upon prescribed device.

In certain examples, access to the patient records can be determined and filtered based upon what type of security access the person reviewing the patient reports has been assigned. For example, a review (e.g., an attending nurse) can have a lower security level associated with their account than another reviewer (e.g., a physician). In such an example, the lower security level viewer can access only a portion of the patient's report. Additional examples of accessing patient reports are provided in the following discussions.

Figure 4A:
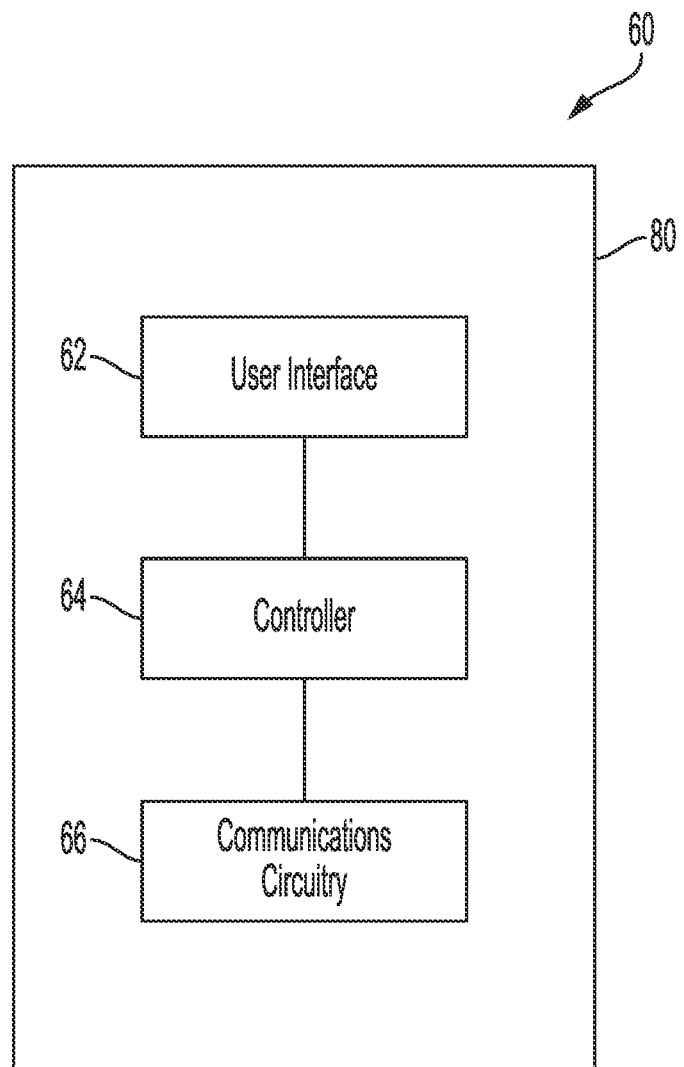
FIGS. 4A and 4B depict schematic drawings of an example patient management system, in accordance with an example of the present disclosure.

With reference to FIG. 4A, the patient management system 60 can include one or more computing and/or electronic devices 80 having a user interface 62, such as a visual display or touch screen, for presenting information to the end user and for receiving selections from the end user, a controller or processor 64 for performing instructions for operating the user interface 62 and for presenting information to the end user, and communications circuitry 66 for receiving the patient reports from the communications network.

In some examples, the patient management system 60 can be distributed in the form of an application (e.g., a mobile device app) that can be executed in a smartphone environment (e.g., Android and/or iOS). For example, a patient management interface for accessing all or some of the portion of the physiological data and/or associated reports in accordance with the principles described herein can be deployed on one or more of a handheld personal digital assistant, tablet device, or a computer workstation.

The electronic device 80 can be a dedicated electronic device configured for the purpose of providing patient reports to the end user. Alternatively, the device 80 can be a multipurpose electronic device such as a computer, laptop computer, tablet PC, smart phone, or similar device configured to execute installed software or to access non-downloadable software from a remote network or the Internet. In some examples, the electronic device can be configured to access a website (e.g., a webpage portal) for organizing, selecting, and viewing the patient reports.

In some examples, the communications circuitry 66 can also send or forward reports to other interested individuals for additional review. For example, the communications circuitry 66 can be configured to transmit reports to co-workers, office staff, or to caregivers (including the patient's relatives) that are responsible for a particular patient. Similarly, the communications circuitry 66 can be used to forward patient reports to other servers or networks, such as to a hospital patient database, hospital pharmacy or inventory database, or other networks, servers, or databases that include and/or store patient information.

Figure 4B:
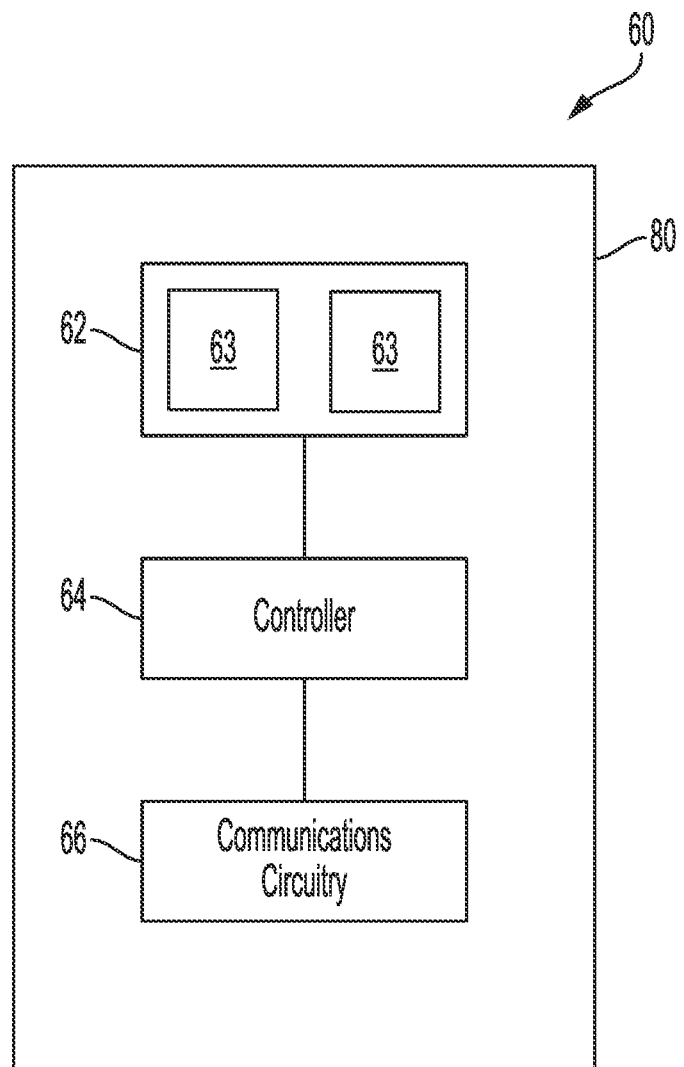

As shown in FIG. 4B, a single electronic device 80 can be configured to run multiple instances 63 of the same application for displaying received physiologic information. In certain implementations, a single instance 63 of the application can be configured to access reports for a single medical device type. As such, by configuring a single electronic device 80 to run multiple instances 63 of the same application, a single reviewer can simultaneously review information related to multiple medical device types.

As shown in FIG. 4B, both instances 63 of the application can be shown on the user interface 62 at the same time. However, based upon the device type, the size and orientation of the user interface 62, the processing capabilities of the controller 64 and the available bandwidth of the communications circuitry 66, the electronic device 80 can be configured to show a single instance 63 of the application at a time, providing the reviewer with the ability to switch between instances to access additional information. For example, if the reviewer is accessing the information on a smartphone, the size of the screen (e.g., user interface 62) and the available processing power (e.g., of controller 64) may result in the reviewer viewing a single instance of the application at a time, and flipping between instances of the application as desired.

It should be noted that two instances 63 of the application running as shown in FIG. 4B is by way of example only. In come implementations, additional instances 63 of the application can be running simultaneously, depending upon how much information the reviewer is accessing (or wants to access) at the time. For example, if a specific physician prescribes three medical devices (for which they can access automated reports), the physician can initiate three instances of the application, one for each medical device they prescribe. The physician can then review all three instances of the application at, or nearly at, the same time.

Figure 5:
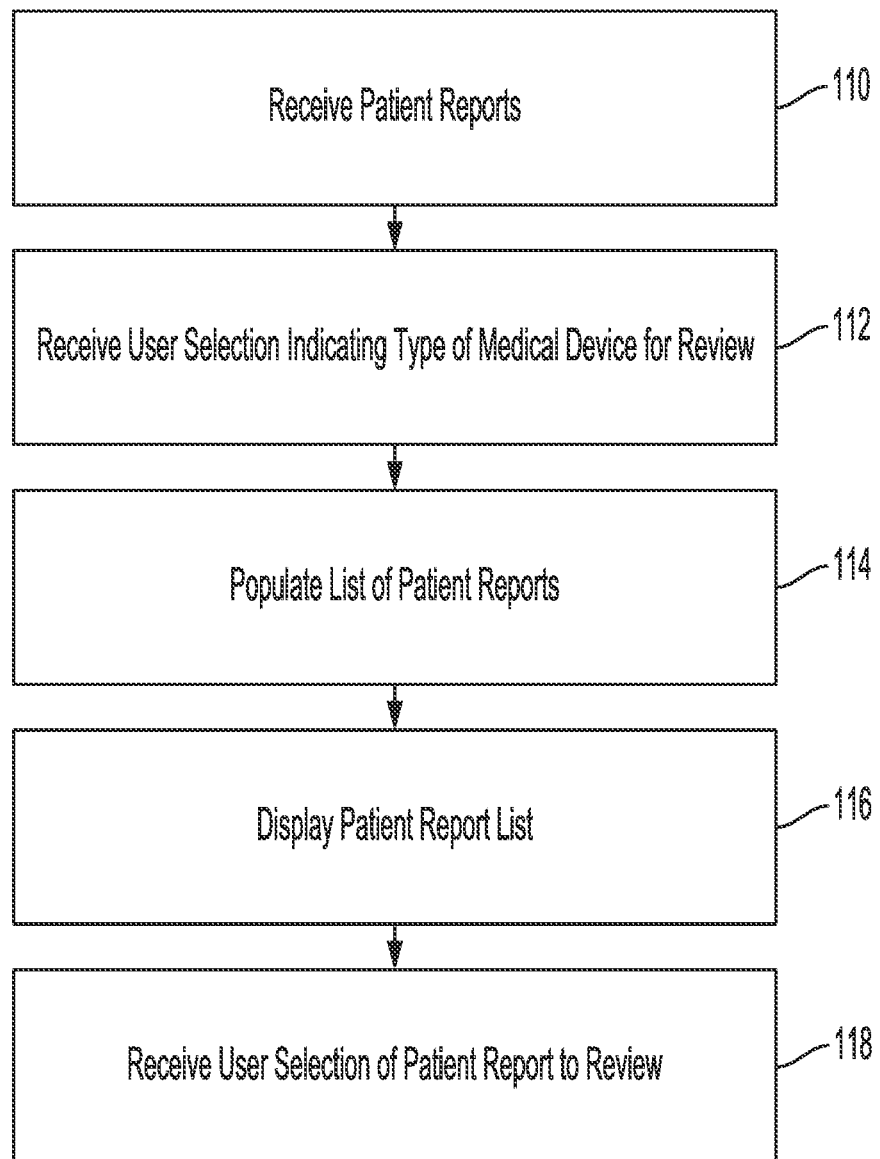
FIG. 5 depicts an example flow chart for displaying patient reports based on monitoring device type, in accordance with an example of the present disclosure.

Display Information Based on Device Type:

In some examples, and with reference to FIG. 5, the end user can select to display a list of patient reports based on the type of medical device that provides the underlying physiological information. More specifically, as shown in FIG. 5, the patient management system can receive 110 patient reports from a plurality of medical devices. In certain implementations, the patient report can identify the type of medical device that provided the physiological information. In some examples, instead of receiving an entire patient report, the patient monitoring system can receive a notification including a list of patient reports that are available on the patient management server, and which can be downloaded from the server for review by the end user when needed. In still other examples, the patient monitoring system can be configured to periodically send requests for available reports to the server and, in response to the request, can receive either all available patient reports as a batch download or can receive the list of available reports as described above.

The patient management system can receive 112 a user selection indicating the type of medical device for review. For example, the end user can select to display patient reports for all patients regardless of type of medical device worn. Alternatively, the end user can select to show only physiological information collected from a particular type of medical device, such as a therapeutic medical device, and not from a second type of medical device, such as a monitoring medical device. Based upon the user selection, the patient management system can populate 114 a list of available patient reports. The patient management system can display 116 the patient report list to the end user. For example, the populated list can be in the form of a patient queue, e.g., an order in which the user (e.g., a physician and/or caregiver) may opt to review and address patients and their related data. For example, the patient queue can include the patient's name or identifying number, along with other information including a number or type of cardiac events reported. The patient management system can receive 118 a user selection of one or more patient reports to review. For example, the end user may select a patient report to review by, for example, clicking on a particular patient name. The end user can also begin with the first name on the list and toggle through each report in sequence.

Figures 6A, 6B:
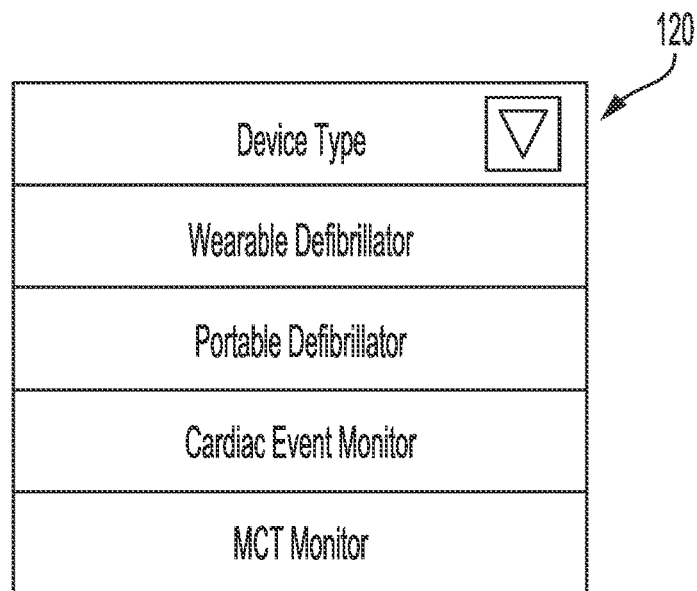
FIG. 6A depicts a schematic drawing of an example drop down menu for selecting a device type, in accordance with an example of the present disclosure.
FIG. 6B depicts a schematic drawing of an example patient queue listing patient reports to be reviewed, in accordance with an example of the present disclosure.

With reference to FIG. 6A, a schematic drawing of a menu that could be shown to a user to select the type of device to review is provided. As shown in FIG. 6A, the end user can be provided with a drop down menu 120 of types or classes of medical devices that the patient monitoring device (e.g., device 20 as shown in FIG. 3) can receive information from. The end user can direct an arrow or other icon over the drop down menu 120 to select the desired class of medical devices.

Figures 6C, 6D:
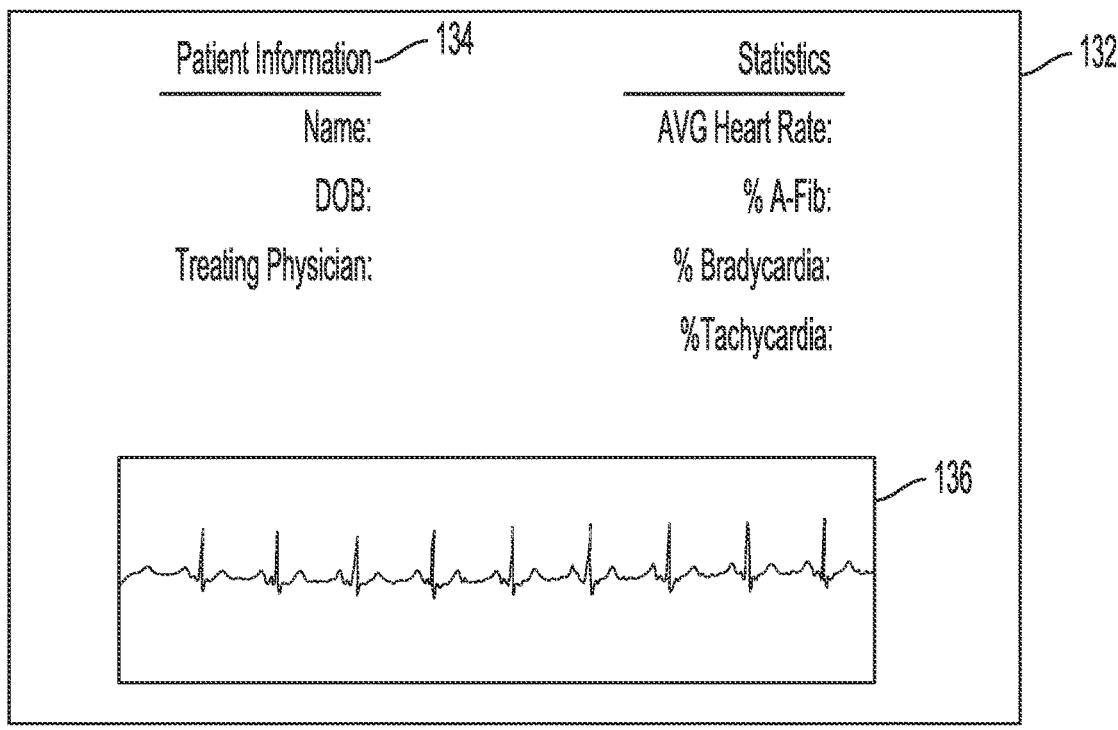
FIG. 6C depicts a schematic drawing of an example patient report for review by an end user, in accordance with an example of the present disclosure.
FIG. 6D depicts another schematic drawing of an example patient queue listing patient reports to be reviewed, in accordance with an example of the present disclosure.

With reference to FIG. 6B, once the selection is made, the end user can be provided with the patient queue 122 showing patient reports available for review and matching the selected criteria (e.g., patient reports for patients assigned the device selected by the user in menu 120). A screen capture with an exemplary patient queue 122 is shown in FIG. 6B. In one example, the patient queue 122 can include a patient name column 124, as well as columns for other patient identifying information, such as patient date of birth 126, treating physician 128, whether or not a treatment has been provided 130 (and number of such treatments, if applicable). The patient queue 122 can also include an indication, for each patient report, of what class or type of medical device provided the physiological information. For example, as shown in FIG. 6B, the indication can be in the form of text, such as a letter (e.g., "T" for therapeutic medical device and "M" for monitoring medical device). In other examples, the indication can be an icon, such as a Lifevest® logo to indicate that the physiological information was recorded by the Lifevest® wearable defibrillator or a picture of the type of medical device that provided the physiological information. Columns related to number or duration of other alerts, patient identified symptoms, and the like can also be included in the list. As shown in FIG. 6D, a patient queue 122 can also include patient reports for patients using different types of medical devices. In that case, the end user is able to easily determine which type of medical device was worn by the patient by viewing the indication or icon associated with each report in the patient queue 122. In certain implementations, a patient's entry in the patient queue 122 can provide an indication that a patient was prescribed multiple devices. For example, a single patient entry can include multiple type indicators (e.g., a T and an M), indicating that the patient transitioned from one device to another. The patient can have two or more associated reports (e.g., one report for each prescribed device) or a single combined report. By providing such a feature, a reviewer such as the treating physician can see any changes in the treatment plan for a specific patient.

In some implementations, a medical device as described herein can be configured to include a cardiac monitor that is optionally fitted with a therapeutic portion (e.g., defibrillation and/or pacing components and electrodes). For example, initially, a patient may be prescribed a cardiac monitor without a therapeutic portion for a period of time during which a caregiver may remotely monitor the patient in accordance with the principles described herein. For example, a caregiver may request to be notified if the patient experiences one or more cardiac or physiologic events, such as, atrial flutter, atrial fibrillation, tachycardia (e.g., based on a configurable trigger between 130 to 190 beats per minute), bradycardia (e.g., based on a configurable trigger between 35 to 50 beats per minute), or a pause. In some examples, the patient may have the ability to initiate a self-reported event, e.g., a skipped beat, shortness of breath, light headedness, racing heart, fatigue, fainting, and/or chest discomfort. Such patient-reported events may also trigger an alert to the caregiver. After a period of time has passed, the caregiver may determine that the patient should be prescribed the therapeutic portion of the medical device, for example, to ensure that the patient is continuously protected in the event of a cardiac arrhythmia. The patient management service 58 is updated with the new device status and type information to indicate that the device has changed to a treatment device (e.g., M can be changed to T). The patient can then be monitored in accordance with predetermined cardiac arrhythmia monitoring criteria, which if detected, can cause the device to issue one or more therapeutic shocks to the patient.

With reference to FIG. 6C, once the end user selects a report to review, a patient report 132 is shown on the patient management system. As discussed above, the patient report may have already been downloaded from the server to the patient management system and stored locally at computer readable memory on the computer device, or the patient report can be accessed directly from the server. The report 132, a schematic drawing of which is shown in FIG. 6C, can include patient identifying information 134, such as the patient name, date of birth and other fields as described above. The report 132 can also include numerical indicators based on physiological information recorded by the medical devices. For example, the report 132 can include numerical values for patient total wear time, percentage of time in atrial fibrillation, percentage of time with bradycardia, percentage of time with tachycardia, average heart rate, most common symptom reported by the patient, number of identified events, and, if applicable, a number of treatments by a therapeutic medical device. In some examples, the report 132 can include graphs 136 of the measured physiological signal (such as a patient ECG) that show physiological reading when events of interest occurred. The graphs 136 can include annotations, edits, or highlighting manually entered by a reviewer at the data analysis site to call attention to particular events of interest. The report 132 can also include other graphs, such as histograms or bar charts, showing, for example, total wear time per day or percentage of time in atrial fibrillation, bradycardia, or tachycardia per day. The report can be received in any of a variety of electronic formats such as, for example, .pdf format or an interactive format such as html.

Figure 7:
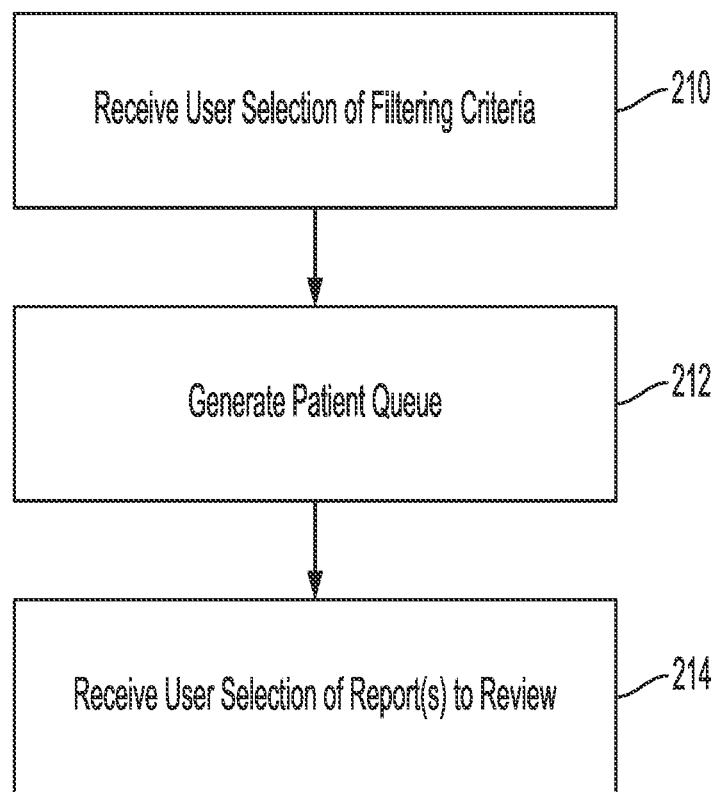
FIG. 7 depicts an example flow chart for viewing patient reports according to a selected event (e.g. triaging reports), in accordance with an example of the present disclosure.

Triage Patient Reports Based on Patient Status:

In some examples and with reference to FIG. 7, the end user can select patient reports shown in the patient queue based, for example, on an identified patient symptom or type of event. In some other examples, the view can be based on when the information and/or report was received or generated, or on the duration or amount of patient data used to generate the patient report (e.g., a previous 24 to 36-hour period, two days, a week, month, or more). In some examples, the patient queue can be organized on the basis of whether a treatment was provided, and, if so, when and in what manner. In some implementations, the physician may triage on the basis of whether a patient has experienced a particular event, such as viewing reports for patients that experienced a glucose spike. In other implementations, a physician can choose to triage reports based on whether or not the associated ECG was edited/reviewed by a technician prior to delivery. In other examples, a physician and/or caregiver can triage on the basis of patient age, gender, patient location (e.g., neighborhood where the patient lives, hospital where the patient is currently admitted, etc.), or on administrative or non-medical factors, such as viewing patient reports for patients that the physician is scheduled to examine or meet with that day.

As discussed above, in one implementation, the patient is able to enter a symptom that he or she is experiencing using a user interface on the therapeutic or monitoring medical device itself. For example, the patient can identify one or more of the following patient symptoms: feeling of a skipped beat, shortness of breath, light headedness, racing heart rate, fatigue, fainting, chest discomfort, weakness, dizziness, and/or giddiness. A patient event can be identified automatically by the medical device and can trigger a data transmission to the remote server or communications network. The event can be confirmed by manual review at the data analysis stage (e.g., by a technician or reviewer as described above). Exemplary events that can be identified using the medical devices include: atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations.

As shown in the sample process illustrated in FIG. 7, the patient management system can receive an end user selection of, for example, a patient symptom, event, or class of events. In certain implementations, the end user can select 210 one or more filtering criteria from a drop down menu including, for example, newly received atrial fibrillation events, newly received tachycardia events, newly received bradycardia events, new patient initiated reports (e.g., reports generated based on a symptom identified by the patient), un-reviewed reports, or other characteristics or fields. Once the selection is received from the user, the patient management system can generate 212 a patient queue that includes patient reports satisfying the selected criteria. Once the patient queue is generated, the patient management system can receive 214 an end user selection for one or more patient reports to review in the manner described above in connection with, for example, FIG. 5. In this way, the end user is able to triage or categorize a number of reports and to review or address only reports that are of particular interest. Once the reports in the initial queue have been reviewed, the end user can select to review other reports by, for example, choosing other selection criteria.

In some examples, the system is configured for the user to enter default selections for viewing or triaging patient reports. The default selections can be stored on a user profile on the patient management system, the patient monitoring server or patient monitoring system. In this way, received reports are automatically triaged or listed in an order determined based on the user's default settings or personal preferences. In this manner, these settings can be saved from session to session and the end user (e.g., physician or caregiver) need not specify them repeatedly.

Figure 8:
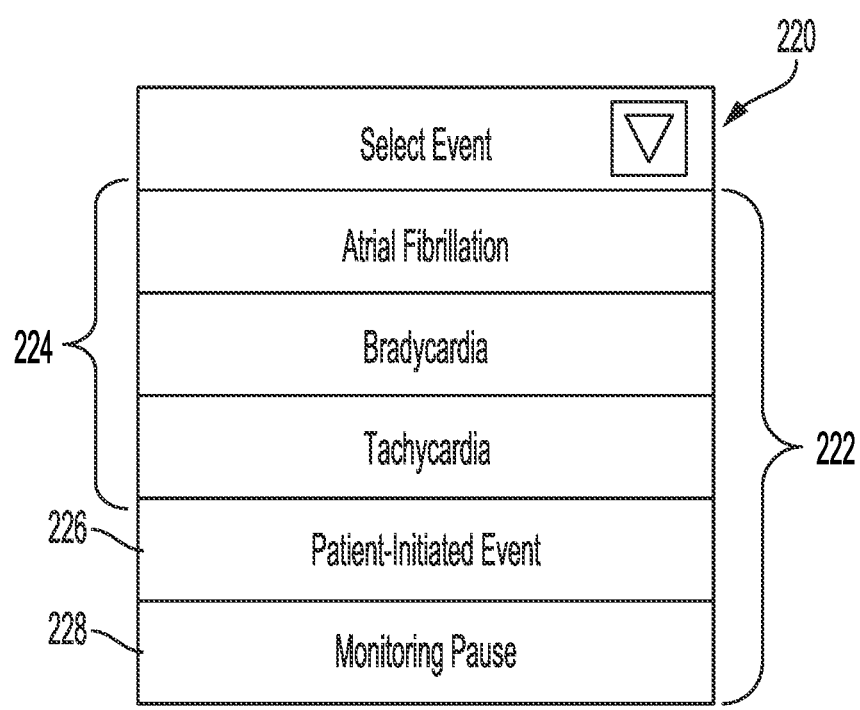
FIG. 8 depicts a schematic drawing of an example drop down menu for selecting events to review, in accordance with an example of the present disclosure.

With reference to FIG. 8, a screen capture of a drop down menu 220 for selecting an event for generating the patient queue is illustrated. As shown in FIG. 8, the patient management system can provide the end user with a list 222 of possible events that can be selected. The list can include, for example, a set of events 224 resulting from physiological event associated with the patient, a patient-initiated event 226, or a caregiver (e.g., a nurse) initiated event 228 such as a pause in monitoring activities. The end user selects the desired event by, for example, moving an arrow or indicia over the desired text. The end user can enter the selection by, for example, clicking on text describing the category of interest. The user can also choose to receive reports based on patient initiated data transfers, which occur when the patient identifies that he or she is experiencing a relevant symptom. The patient queue is then generated. As discussed above, in connection with FIG. 6B, the user can review the patient queue and select to view reports for specific patients. The end user can also review all reports in the patient queue in order. An exemplary patient report that can be reviewed by the end user is illustrated, for example, in FIG. 6C.

Figure 9:
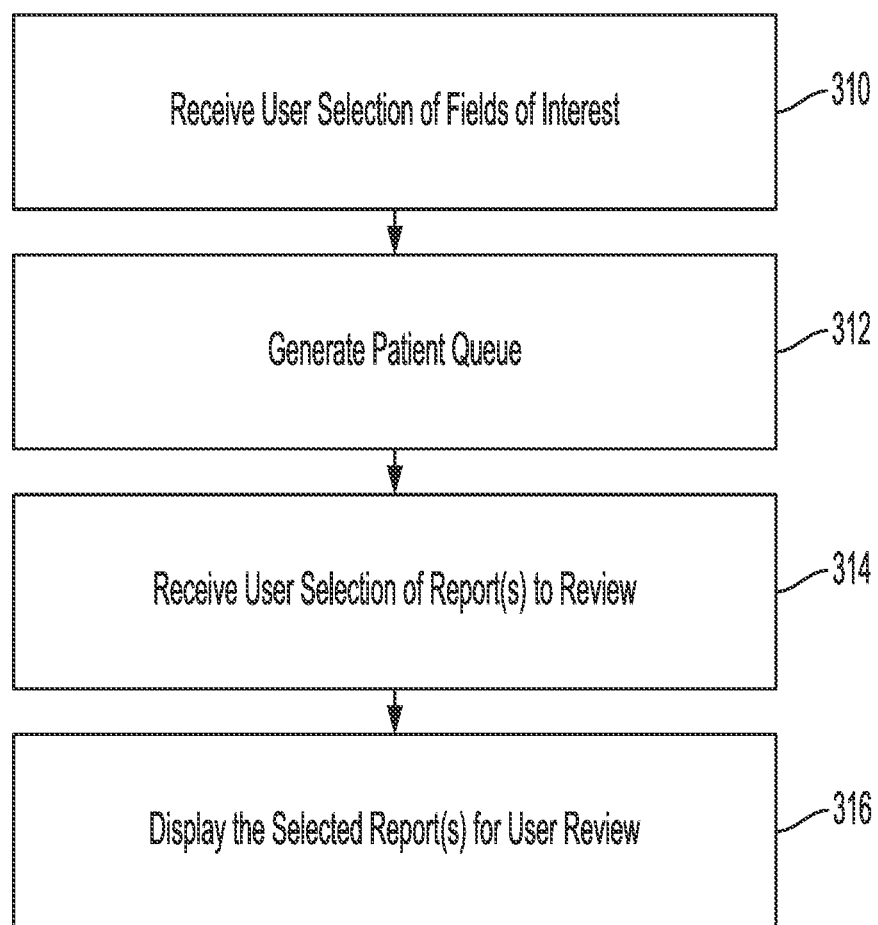
FIG. 9 depicts an example flow chart for customizing patient reports to review, in accordance with an example of the present disclosure.

Patient Report Customization:

In some examples and with reference to FIG. 9, the end user can also customize the types or fields of information that are displayed in a patient report for a particular patient or class of patients. For example, the end user can set his/her preferences within a user account. In this manner, the information is associated with the end user profile and the end user does not have to re-enter his or her preferences again.

For example, as shown in FIG. 9, the patient management system can provide the end user with a list of fields of information. The end user can select fields of particular interest. The user's selections can be stored in a user profile and can be applied to each received patient report so that the user is not required to re-enter each selection for each report or during each new session. As such, when the user starts a new session, the patient management system can receive 310 the user selection of the one or more fields of interest.

Once the field or fields of interest are manually or automatically selected, and received by the patient management system, the patient management system can generate 312 the patient queue including the desired customized patient reports (as determined based upon the user selected fields of interest). In some examples, the patient queue can be ordered or arranged based on a particular information field. For example, patient reports showing the highest levels or rates of a particular value can be shown first in the list. Accordingly, in one example, patient reports for patients that had the greatest percentage of time in atrial fibrillation, bradycardia, and/or tachycardia are shown first in the patient queue. Patient reports reporting a lower percentages of time in atrial fibrillation, bradycardia, and/or tachycardia appear lower in the patient queue. As in previously described examples, the patient management system can receive 314 an end user selection of one or more generated reports to review. Based upon the selection, the patient management system displays 316 the selected one or more reports for the user to review.

In some examples, the selection of which fields to include in a customized report can be determined automatically by the patient management system. Similarly, the selection of which patient reports appear in the patient queue can also be automatically determined based upon, for example, what type of viewer application the end user is using or an access level that has been assigned to the user.

For example, the patient management system can select information fields based on the user reviewing the report (e.g. the user's role and their associated level of access). For example, if the user is a prescribing physician, the report can include information showing changes in patient condition over time (e.g., information showing an evolution of patient status). However, if the end user is a nurse or caregiver, the report can only include information about the patient's current condition so that the nurse or caregiver can provide appropriate care. As such, the nurse does not have access to the entire patient record that is available to the physician.

The patient management system can also select information fields or reports to review based on the user's location. For example, if the end user is a prescribing physician, the monitoring device can identify the physician's current location and can only provide reports for patients that the physician sees at the identified location. For example, if the treating physician sees patients in a number of different hospitals, the patient management system can be configured to only provide patient reports for patients in the hospital where the physician is presently working. The patient management system can be configured to selectively filter the patient records database based upon a location field (e.g., a field including a name or code representing the hospital or other facility the patient is currently staying at) to provide a physician with a listing of their patients at one specific location. In addition, the patient management system can be configured to automatically forward patient reports to nurses and/or support staff at the particular hospital where the physician is working, but not to other hospitals where, for example, the physician is at other times.

Figure 10:
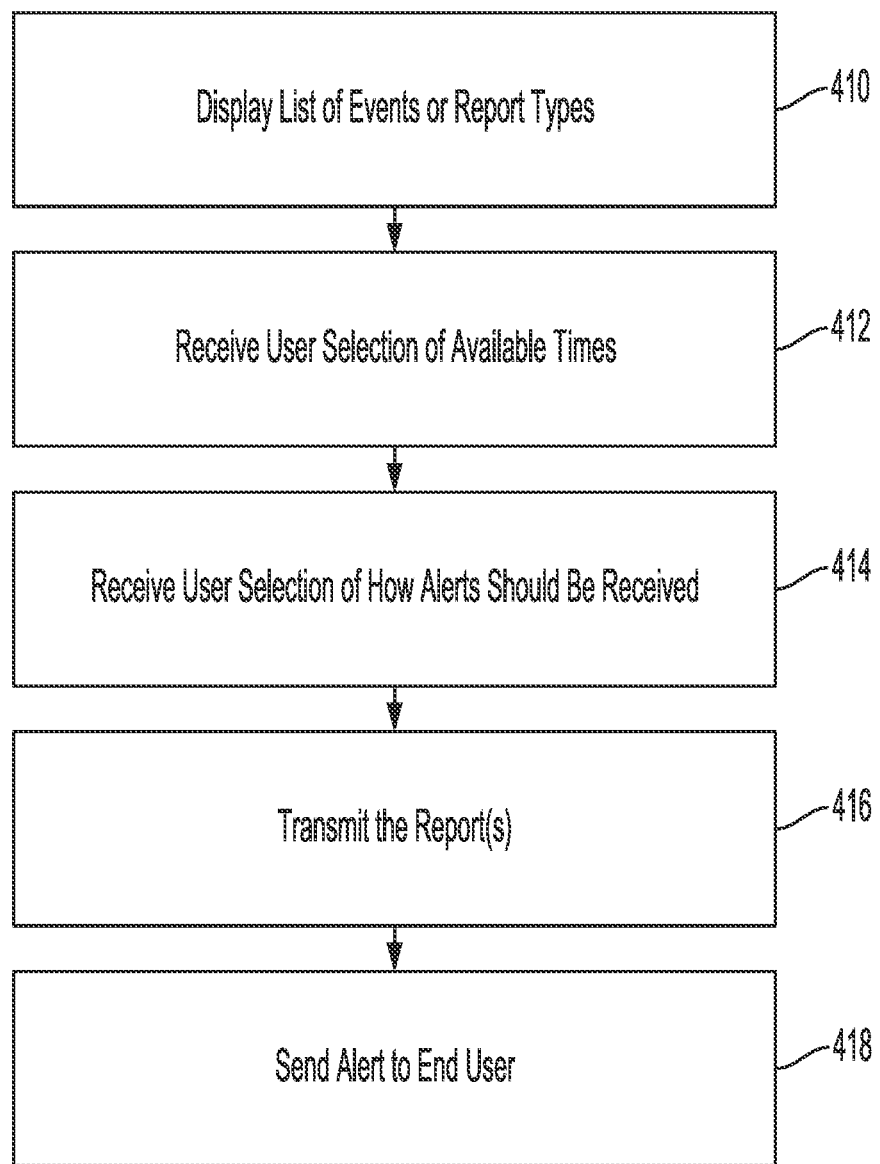
FIG. 10 depicts an example flow chart for setting up alerts or notifications based on received patient reports, in accordance with an example of the present disclosure.

In some examples, the patient management system is configured to allow the end user to set up alerts for specific patients or for a subset or class of patients. As discussed above in connection with triage of patient reports, the alert fields selected by the user can be stored in a user profile and applied to all received patient reports. In this manner, the user is not required to re-enter information or selections for each session or for each individual patient. With reference to FIG. 10, the patient management system can display 410 a list of events or types of patient reports that can be received using the patient management system for user review. For example, the list can include: receipt of a new atrial fibrillation report, receipt of a new tachycardia event report, receipt of a new pause event report, receipt of a new patient-initiated event report, or a report indicating that a patient has transitioned to inactive status. The end user can select any or all of these alert options by, for example, checking a box associated with each item. In another implantation, an alert can be based on performance or function of the medical device or monitoring device. For example, the user may select to receive an alert each time that a patient experiences a specific type of event or, for a patient using a therapeutic medical device, each time that the device provides treatment to the patient.

With continued reference to FIG. 10, the patient management system can receive 412 a user selection of available times (e.g., times when the physician elects to receive alerts or notifications). For example, the end user can select to only receive alerts or notifications during weekdays, or during normal business hours. In some examples, the user can also select to receive certain reports any time (e.g., 24 hours a day), such as reports indicating that treatment was provided to a patient, and to receive other types of reports, such as more standard daily or weekly status reports, only during normal business hours. For example, the end user can set his/her alert preferences within his or her user account such that the end user's preferences are associated with the end user's profile and the end user does not have to re-enter his or her preferences again.

The patient management system can also receive 414 a user selection indicating how the alerts and/or notifications should be received. For example, the end user can receive an alert or notification by email, voice message, fax, SMS text message, and/or by email. Based upon the time selected and how the alert and/or notifications should be received, the patient management system can transmit 416 one or more reports to the patient management system via the communications network. If a report is received that matches the selected criteria, the patient management system can send 418 an alert or notification to the end user using the selected communications mode or modality at the selected time. As discussed above, the monitoring device can also automatically forward reports to the nurses or hospital support staff responsible for treating a particular patient. In the case in which a physician works at multiple locations or hospitals, the monitoring device determines which patients are located at a particular location and forwards the alert or notification to the correct individuals.

Figure 11:
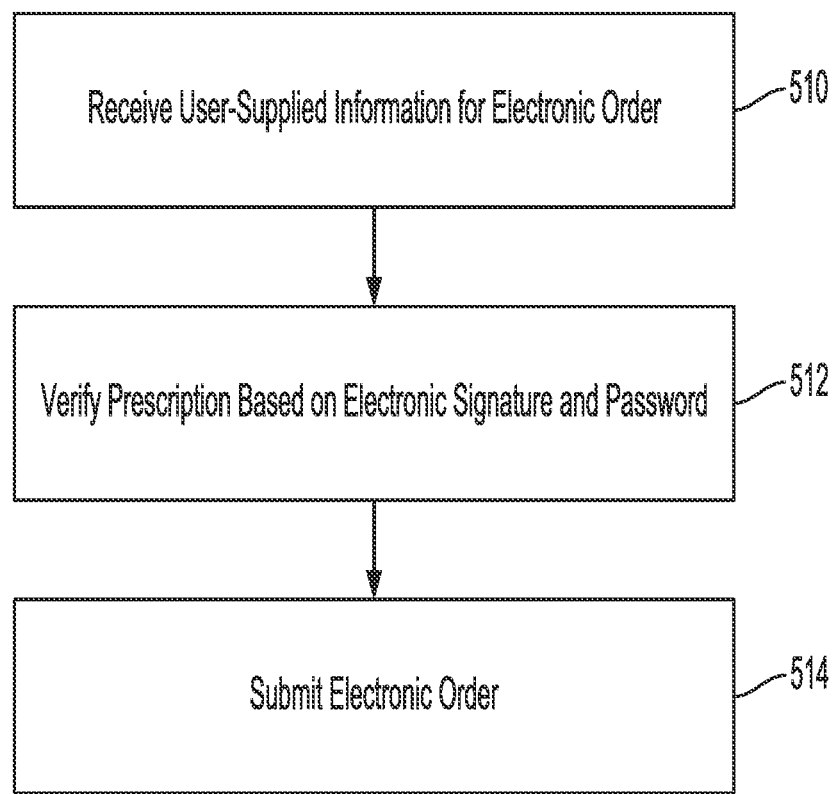
FIG. 11 depicts an example flow chart for submitting an electronic order for a cardiac monitoring device, in accordance with an example of the present disclosure.

Electronic Ordering:

With reference to FIG. 11, the patient management system can also be configured to allow the end user to directly order a medical device for treatment of a patient. In certain embodiments, the patient management system can be configured to receive 510 information related to an electronic order. For example, the end user, such as a physician, can fill out an electronic order form for a therapeutic or monitoring medical device. For example, the electronic order form may be displayed to an authorized person (e.g., a physician, nurse, other caregiver and/or their designees), via a computer, handheld tablet or a fixed terminal tablet, a smartphone, a personal digital assistant, or other such computing device. For example, the electronic order form may be implemented as an application or an "app" on such a computing computer. As an example, in the Android™ platform, an app carrying out the functionality as described herein may be downloaded from an app store. In some examples, an app or application deployed on a computing device can be configured to carry out some or all of the steps of an electrode order process as described below. For instance, an electronic order for a therapeutic or monitoring medical device can be initiated by a first authorized person (e.g., a remote technical support person). A second authorized person, e.g., a person with signatory authority, can then log into the electrode order application or app, and electronically sign or cause the order to be approved. In such implementations, the patient management system can include a remote server for communicating with one or more computing devices in the field, e.g., hosting a database and/or related functionality to support the electronic order features described herein. In certain implementations, the order form can include locations for entering prescriber information to confirm that the end user has proper credentials to order a particular monitoring device. The order form can also include locations for entering patient information for the patient to be monitored, monitor information and settings, indications for monitoring, and insurance information. For example, monitor information and settings can include a particular service type (e.g., either mobile cardiac telemetry or cardiac event monitoring), logistics such as whether the physician will provide the monitor to the patient directly or whether the monitor will be shipped directly to the patient, as well as default or threshold values indicating when an alert or report should be generated. For example, a bradycardia threshold value can be set to measurements below 30 beats per minute. A tachycardia threshold value can be set at above 150 beats per minute. In the indications for monitoring section, the physician can select particular events to be identified including, but not limited to, atrial fibrillation, atrial flutter, and other conditions or events.

For security, the end user can enter an electronic signature and password to verify the prescription. The patient management system can receive the electronic signature and password, and verify 512 the prescription. The end user can select to submit the order and, in response, the patient management system can submit 514 the electronic order to, for example, the patient management server. Once the order is submitted, the end user can provide a cardiac monitor device directly to the patient and cardiac monitoring can be commenced. Alternatively, the monitor can be shipped to the patient.

It is noted that the above-described electronic ordering protocol can be used for cardiac and other monitoring devices. However, for treatment devices, it is likely that the patient will need to receive the device from a service representative or another service provider associated with the device manufacturer and/or provider. In that case, the end user can fill out and submit the electronic order form. The patient will then be contacted by the service representative and provided with the appropriate therapeutic device.

Application Specific Reports:

As noted above, a patient management system can be configured to run one or more applications for receiving and viewing patient reports, based upon the type of application a reviewer (e.g., a physician) has, which can limit the amount or type of information the reviewer has access to. For example, a physician can subscribe to a vendor specific application that is configured to provide patient report information for a device manufactured and distributed by that vendor. For other devices and vendors, the physician can subscribe or purchase access to additional applications for viewing patient reports for those additional devices. In certain implementations, an application can be configured to automatically update a patient report, or list of patient reports, if that patient is subscribed a new device. For example, patient data can be maintained in a data structure such as a database or folder structure stored on a central server (such as patient management server 58). The database or folder structure can be organized such that patient records (or pointers to patient records) are organized by device type. For example, the server can include a database table for each type of device. Patient records can then be organized within each table by more specific information such as patient name, date of birth, attending physician and other similar information.

Figure 12:
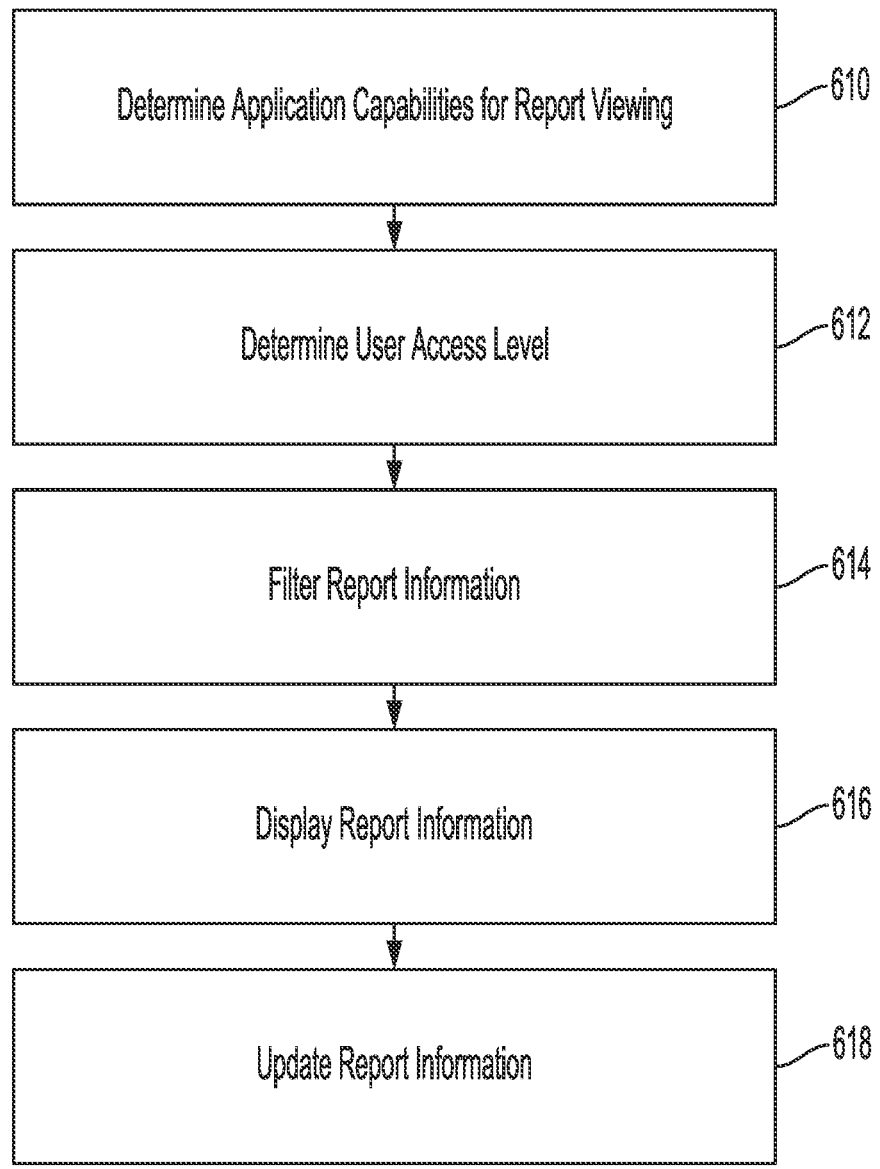
FIG. 12 depicts an example flow chart for information filtering based upon application and user access levels, in accordance with an example of the present disclosure.

As shown in FIG. 12, one or more patient reports can be filtered and delivered, and/or updated, by the patient management system. For example, a reviewer can login to a specific application to access one or more patient records. As noted above, the application can be device specific and, as such, can be configured to display only patient records associated with a specific device. For example, the application can be configured to only access and display patient records for patients that have been prescribed a wearable defibrillator. In such an example, the patient management system can determine 610 the application capabilities and permissions for viewing one or more patient reports. The patient management system can also determine 612 a user access level for the reviewer requesting access to the patient reports. For example, as noted above, the patient management system (and/or the application used by the reviewer) can be configured to limit access to the patient reports and related information based upon an associated access level of the requesting reviewer. Based upon one or more of the application being used and the reviewer's associated access level, the patient management system can filter 614 the report information such that the reviewer is only provided with information they have access and/or permission to view. The patient management system can then provide or display 616 the filtered reports and related information to the end user, e.g., via the patient management system.

As noted above, based upon what type of device a patient has been prescribed (e.g., a therapeutic device or a monitoring device), the patient's record can be stored in a specific location at the patient management server (e.g., in a specific table of a database stored on the server). In certain implementations, if a patient's treatment plan changes such that the patient transitions from one device to another (e.g., from a cardiac monitoring device to a wearable defibrillator), the patient's record may be updated and moved in the server's storage accordingly (or, in some examples, a pointer to the patient's record can be updated and moved accordingly within, for example, the database). In response to such an update, the patient management system can update 618 its record information. As such, a physician or other reviewer can potentially access the updated record (e.g., if the patient has now been prescribed a device the physician can access the patient reports for) via the report viewing application. Such an arrangement can provide the reviewer with a tool for viewing a patient's record in or at near real-time in response to a patient being prescribed a new device.

It should be noted that, while the discussion of FIG. 12 described one or more report viewing applications that are device specific, a single application (as is described in detail above) that is configured to view information for patient records across multiple devices can also be configured to update a patient report in or at near real-time when a patient is prescribed a new medical device. Again, such an arrangement provides for a physician or other reviewer to accurately view the patient's entire treatment plan including changes in devices and any events that occurred prior or subsequent to the changing of the medical device prescription. In certain implementations, when running multiple instances of the same application, each instance configured to display information related to a single medical device type, a change in a patient's device type can be represented by removing the patient's record from a first instance of the application (associated with, for example, their previous device) and adding the patient's report to a second instance of the application (associated with, for example, the patient's newly prescribed device).

The embodiments have been described with reference to various examples. Modifications and alterations will occur to others upon reading and understanding the foregoing examples. Accordingly, the foregoing examples are not to be construed as limiting the disclosure.

We claim:

1. A patient management system for providing patient queues of patient reports to users, the patient management system comprising:
communications circuitry configured to
receive first physiological information from a plurality of monitoring medical devices being worn by a first plurality of patients, wherein each of the monitoring medical devices is configured to sense one or more predetermined physiological parameters of its respective patient, and
receive second physiological information from a plurality of therapeutic medical devices being worn by a second plurality of patients, wherein each of the therapeutic medical devices is configured to monitor its respective patient for a predetermined physiological condition and provide a treatment to the respective patient upon detecting the predetermined physiological condition; and
at least one processor in electronic communication with the communications circuitry and configured to
process the first physiological information to prepare a plurality of monitoring patient reports for the first plurality of patients,
process the second physiological information to prepare a plurality of therapeutic patient reports for the second plurality of patients,
generate a patient queue based on the pluralities of monitoring and therapeutic patient reports, and
provide the patient queue to an end user computing device via the communications circuitry.

2. The patient management system of claim 1, wherein the first physiological information and the second physiological information comprise information related to at least one of heart rate, heart rate variability, premature ventricular contraction (PVC) burden, PVC counts, atrial fibrillation, heart rate turbulence, QRS height, QRS width, cosine R-T, corrected QT interval, QT variability, T wave width, T wave alternans, T-wave variability, ST segment changes, fractionated QRS, or fractionated T wave content.

3. The patient management system of claim 1, wherein the first physiological information and the second physiological information comprise information related to at least one of ECG data, heart sounds data, lung fluid data, patient thoracic impedance data, pectoral impedance data, blood pressure data, or blood oxygen level data.

4. The patient management system of claim 1, wherein at least one of the first physiological information or the second physiological information comprises patient symptom data.

5. The patient management system of claim 4, wherein the patient symptom data comprises patient-reported symptoms, each patient-reported symptom identified by one of the first or second pluralities of patients via a user interface of one of the plurality of monitoring medical devices or the plurality of therapeutic medical devices.

6. The patient management system of claim 5, wherein each of the patient-reported symptoms comprises a selection from one or more of a skipped beat, a shortness of breath, light-headedness, a racing heart rate, fatigue, fainting, chest discomfort, weakness, dizziness, or giddiness.

7. The patient management system of claim 1, wherein each of the monitoring medical devices comprises a mobile monitoring cardiac device.

8. The patient management system of claim 1, wherein each of the therapeutic medical devices comprises at least one of a wearable cardioverter defibrillator or an external pacing device.

9. The patient management system of claim 1, wherein the at least one processor is further configured to generate the patient queue based on at least one of an identified patient symptom or a type of event in the pluralities of monitoring and therapeutic patient reports.

10. The patient management system of claim 9, wherein at least one of the first physiological information or the second physiological information comprises patient symptom data, the patient symptom data comprising patient-reported symptoms, and wherein at least one of the plurality of monitoring patient reports or the plurality of therapeutic patient reports comprises the patient-reported symptoms.

11. The patient management system of claim 10, wherein each of the patient-reported symptoms is identified by one of the first or second pluralities of patients via a user interface of one of the plurality of monitoring medical devices or the plurality of therapeutic medical devices.

12. The patient management system of claim 10, wherein each of the patient-reported symptoms comprises a selection from one or more of a feeling of a skipped beat, shortness of breath, light-headedness, a racing heart rate, fatigue, fainting, chest discomfort, weakness, dizziness, or giddiness.

13. The patient management system of claim 9, wherein the type of event comprises whether a treatment was provided to a given patient of the first or second pluralities of patients.

14. The patient management system of claim 9, wherein the type of event comprises whether a given patient of the first or second pluralities of patients experienced at least one of atrial fibrillation, bradycardia, tachycardia, an atrial-ventricular block, Lown-Ganong-Levine syndrome, an atrial flutter, a sino-atrial node dysfunction, cerebral ischemia, syncope, an atrial pause, or heart palpitations.

15. The patient management system of claim 1, wherein the at least one processor is configured to generate the patient queue further based on at least one of patient age, patient gender, patient location, or an administrative factor.

16. The patient management system of claim 1, wherein the at least one processor is further configured to
receive a default selection for triaging patient reports from the end user; and
store the default selection on a user profile for the end user.

17. The patient management system of claim 16, wherein the at least one processor is configured to generate the patient queue further based on the stored default selection.

18. The patient management system of claim 1, wherein the at least one processor is configured to generate the patient queue further based on an information field of at least one of the plurality of monitoring patient reports or the plurality of therapeutic patient reports.

19. The patient management system of claim 18, wherein the information field comprises an amount of time a given patient of the first plurality of patients or the second plurality of patients spent in at least one of atrial fibrillation, tachycardia, or bradycardia.

20. The patient management system of claim 1, wherein the at least one processor is further configured to generate an alert for at least one of a specific patient or for a subset of patients of at least one of the first or second pluralities of patients.

* * * * *